United States Patent [19]

Sprecker et al.

[11] Patent Number: 4,636,333
[45] Date of Patent: Jan. 13, 1987

[54] ALKOXY-SUBSTITUTED POLYHYDROINDAN CARBOXALDEHYDES

[75] Inventors: Mark A. Sprecker, Sea Bright; William L. Schreiber, Jackson; Futoshi Fujioka, Wanamassa; Richard M. Boden, Ocean; Manfred H. Vock, Locust; Patrick Whelan, Matawan; Marie R. Hanna, Hazlet, all of N.J.

[73] Assignee: International Flavors & Fragrances Inc., New York, N.Y.

[21] Appl. No.: 837,386

[22] Filed: Mar. 7, 1986

Related U.S. Application Data

[60] Division of Ser. No. 712,164, Mar. 15, 1985, which is a continuation-in-part of Ser. No. 528,568, Sep. 1, 1983, Pat. No. 4,541,949.

[51] Int. Cl.⁴ .................................................. A61K 7/46
[52] U.S. Cl. .................................................. 252/522 R
[58] Field of Search .................................... 252/522 R

[56] References Cited

U.S. PATENT DOCUMENTS 4,541,949  9/1985  Sprecker et al. ............... 252/522 R Primary Examiner—Anton H. Sutto
Attorney, Agent, or Firm—Arthur L. Liberman

[57] ABSTRACT

Described is a mixture of polyhydroindan carboxaldehydes defined according to the structure:

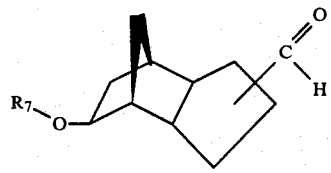

wherein $R_7$ represents a moiety selected from the group consisting of methyl and isopropyl prepared by means of reacting bicyclopentadiene with a lower alkanol in the presence of a Lewis acid in order to form a mixture of compounds defined according to the structure:

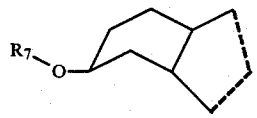

and then reacting the resulting ether with carbon monoxide and hydrogen in the presence of an "oxo" reaction catalyst.

6 Claims, 25 Drawing Figures

IR SPECTRUM OF FRACTION 4 FOR EXAMPLE I

GLC PROFILE FOR EXAMPLE IV. CRUDE

GLC PROFILE FOR EXAMPLE II. CRUDE

FIG. 4 NMR SPECTRUM FOR EXAMPLE II.

IR SPECTRUM FOR EXAMPLE II.

NMR SPECTRUM FOR EXAMPLE III.

IR SPECTRUM FOR EXAMPLE III.

NMR SPECTRUM FOR EXAMPLE IV.

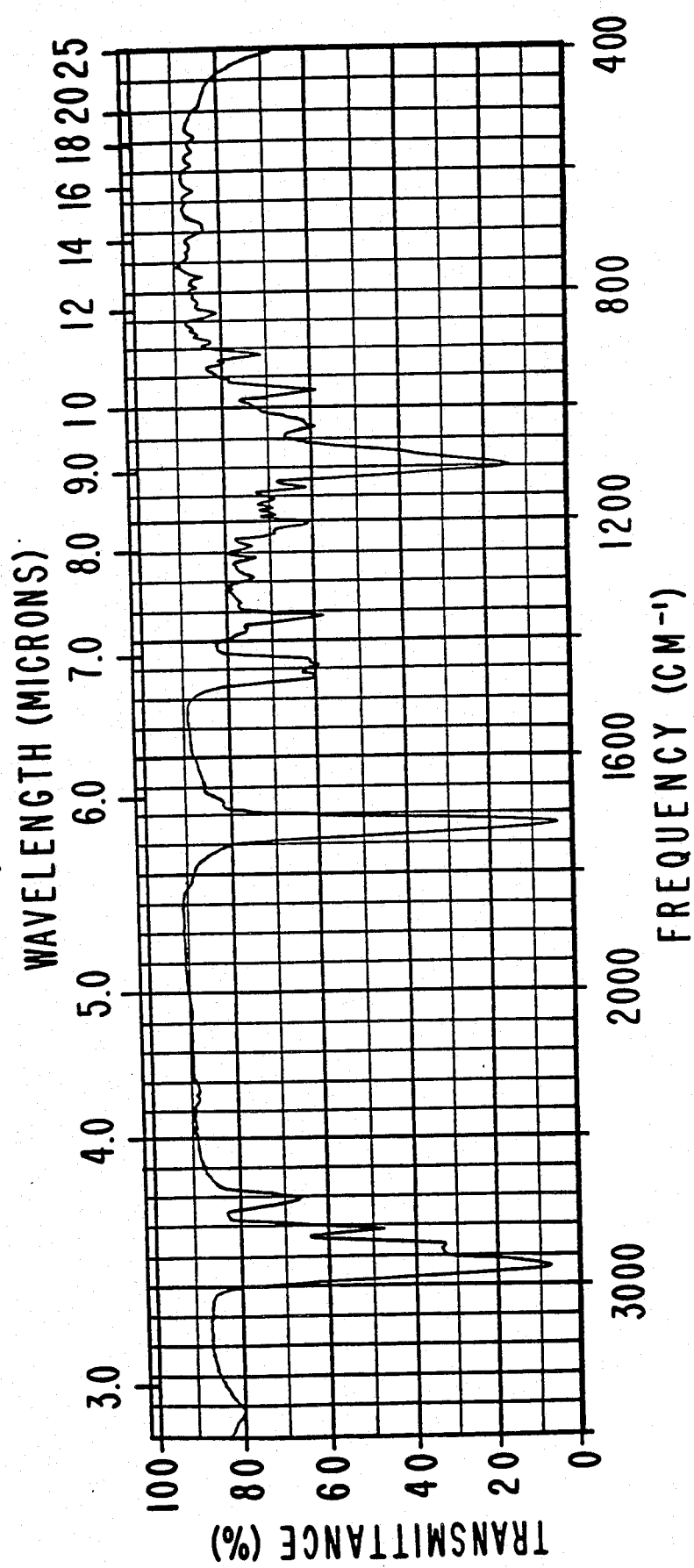

GLC PROFILE FOR EXAMPLE VI. CRUDE

GLC PROFILE FOR EXAMPLE V. CRUDE

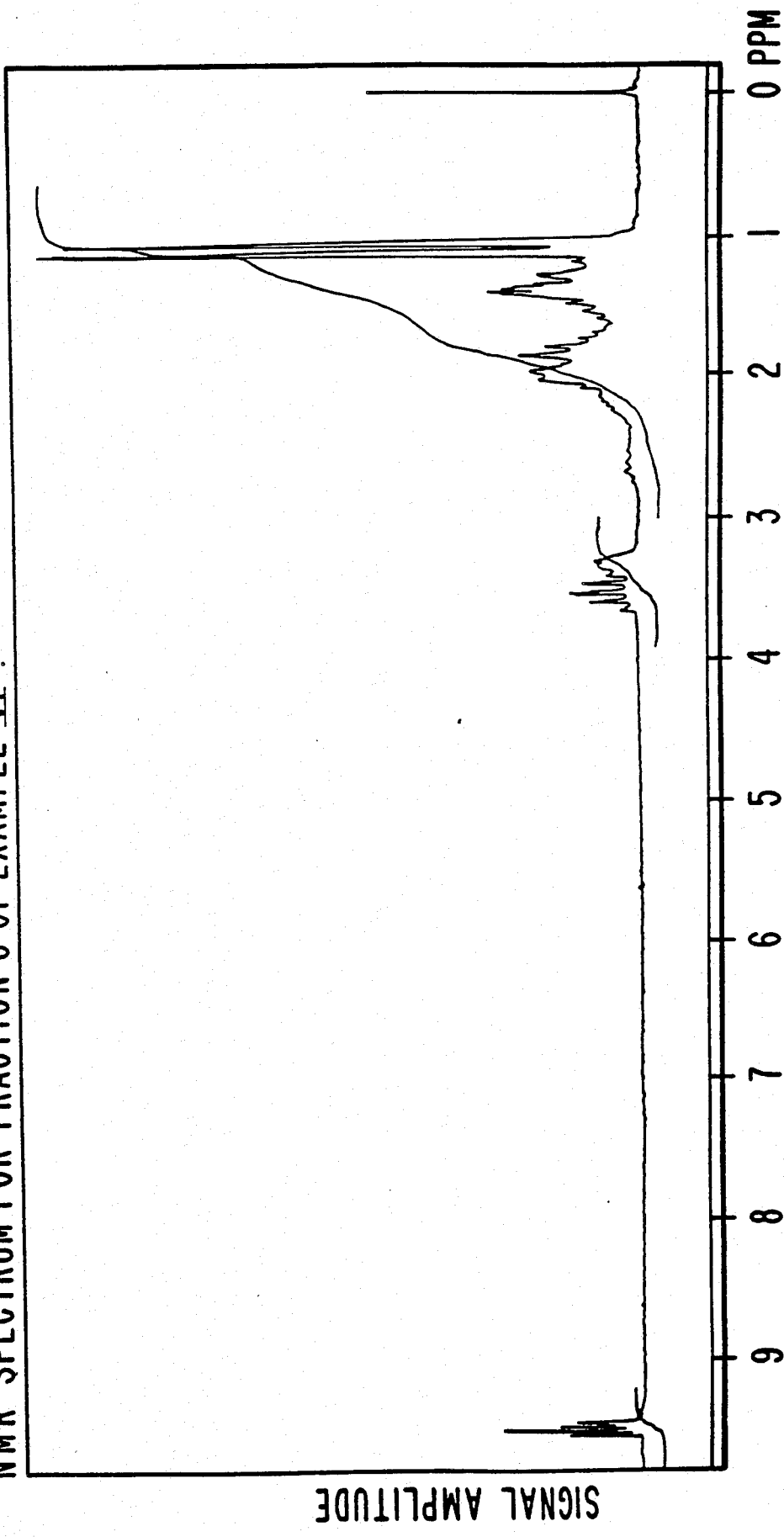

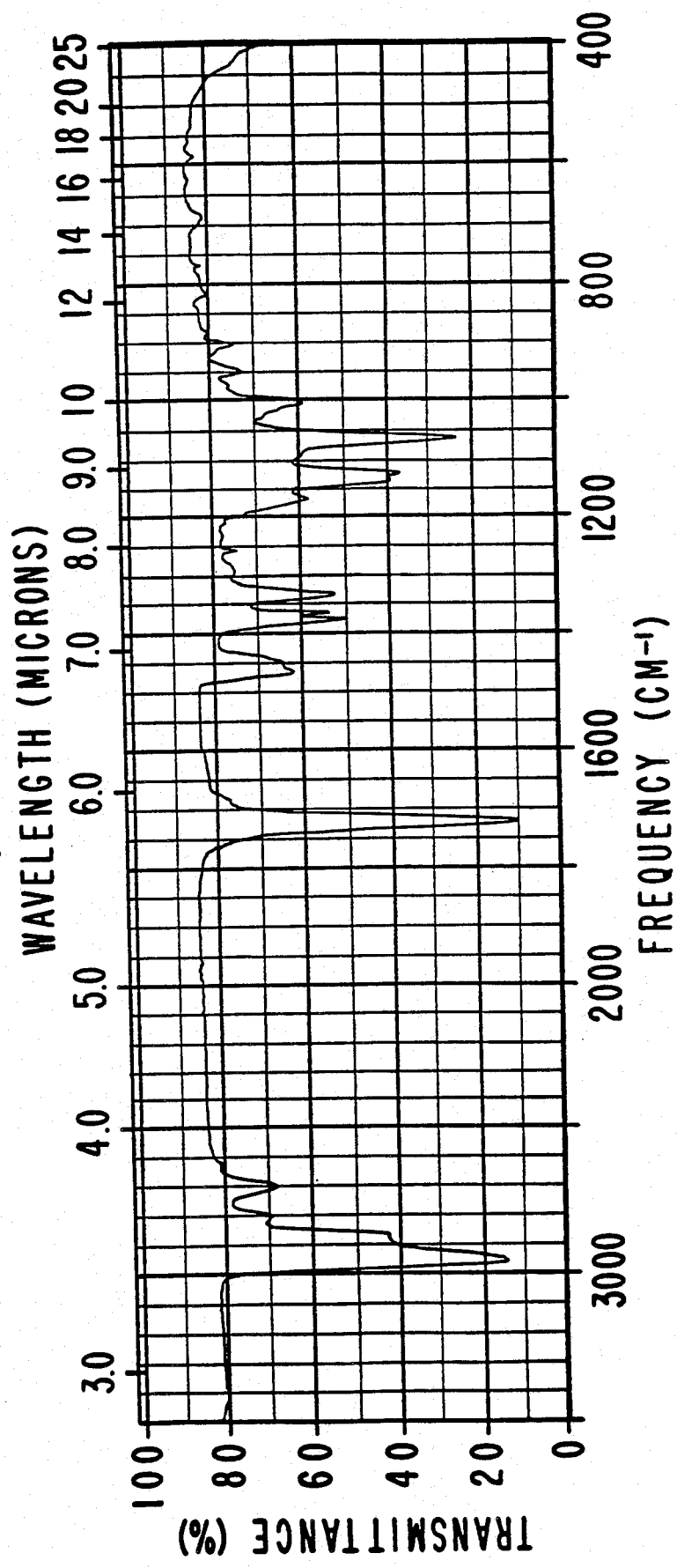

GLC PROFILE FOR FRACTION 4 OF EXAMPLE VIII.

GLC PROFILE FOR EXAMPLE VII. CRUDE

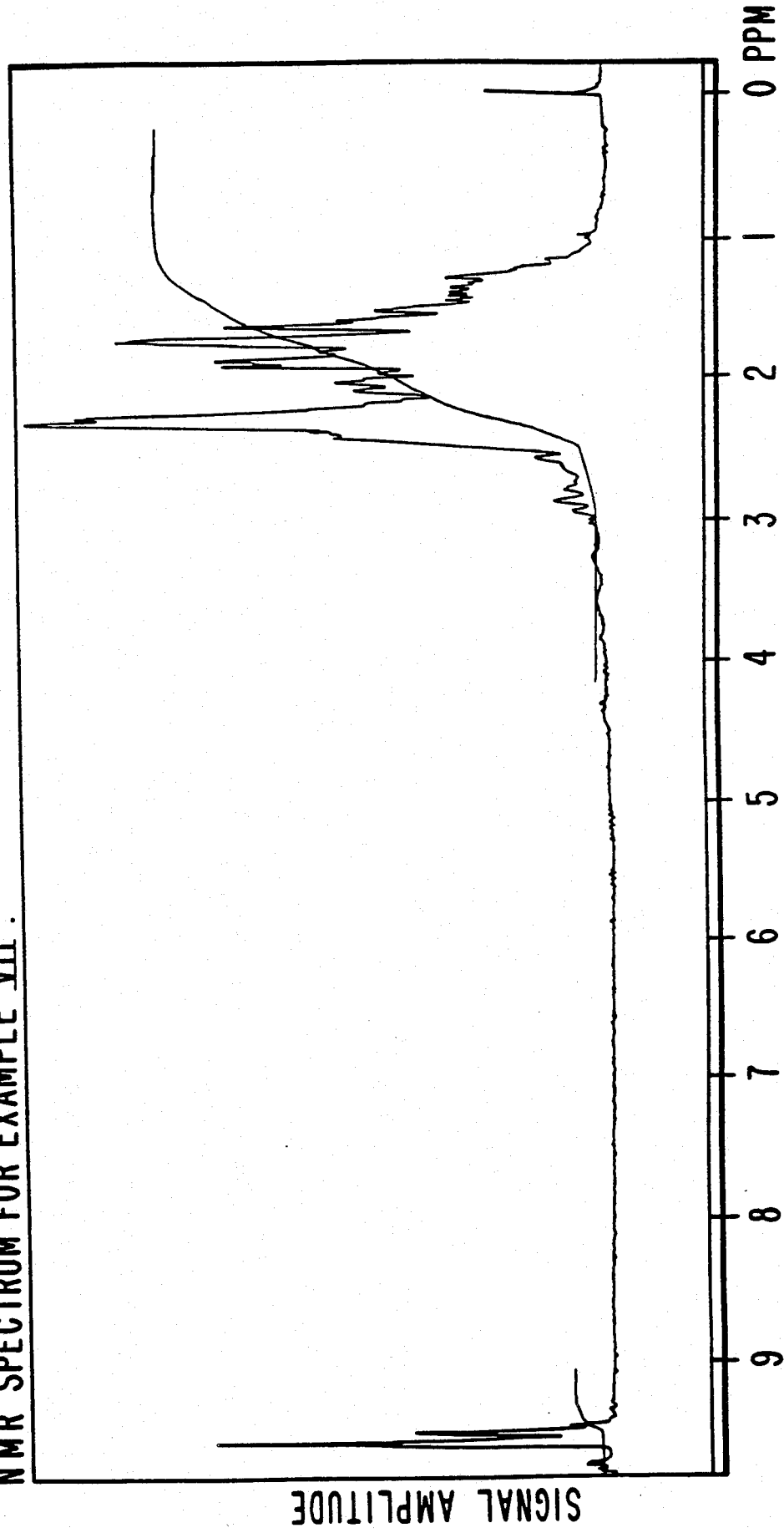

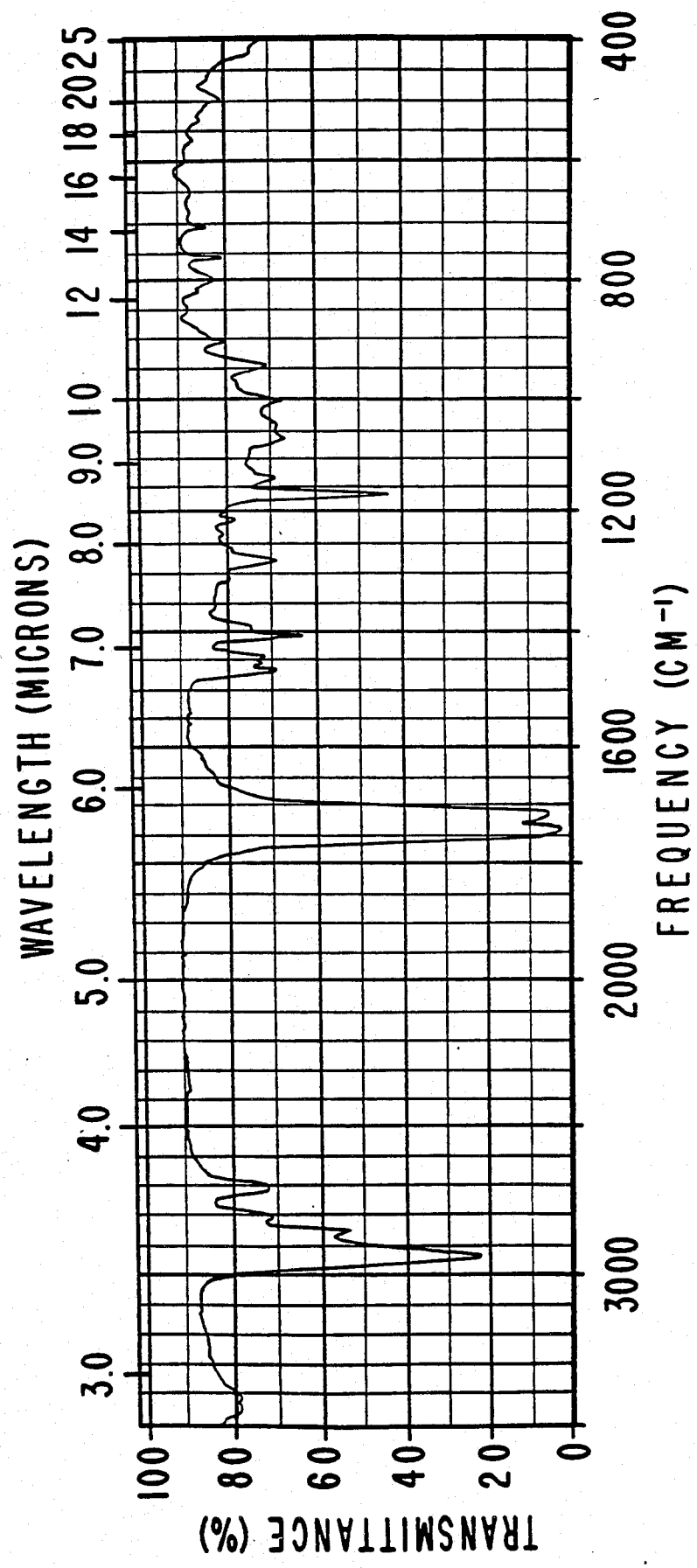

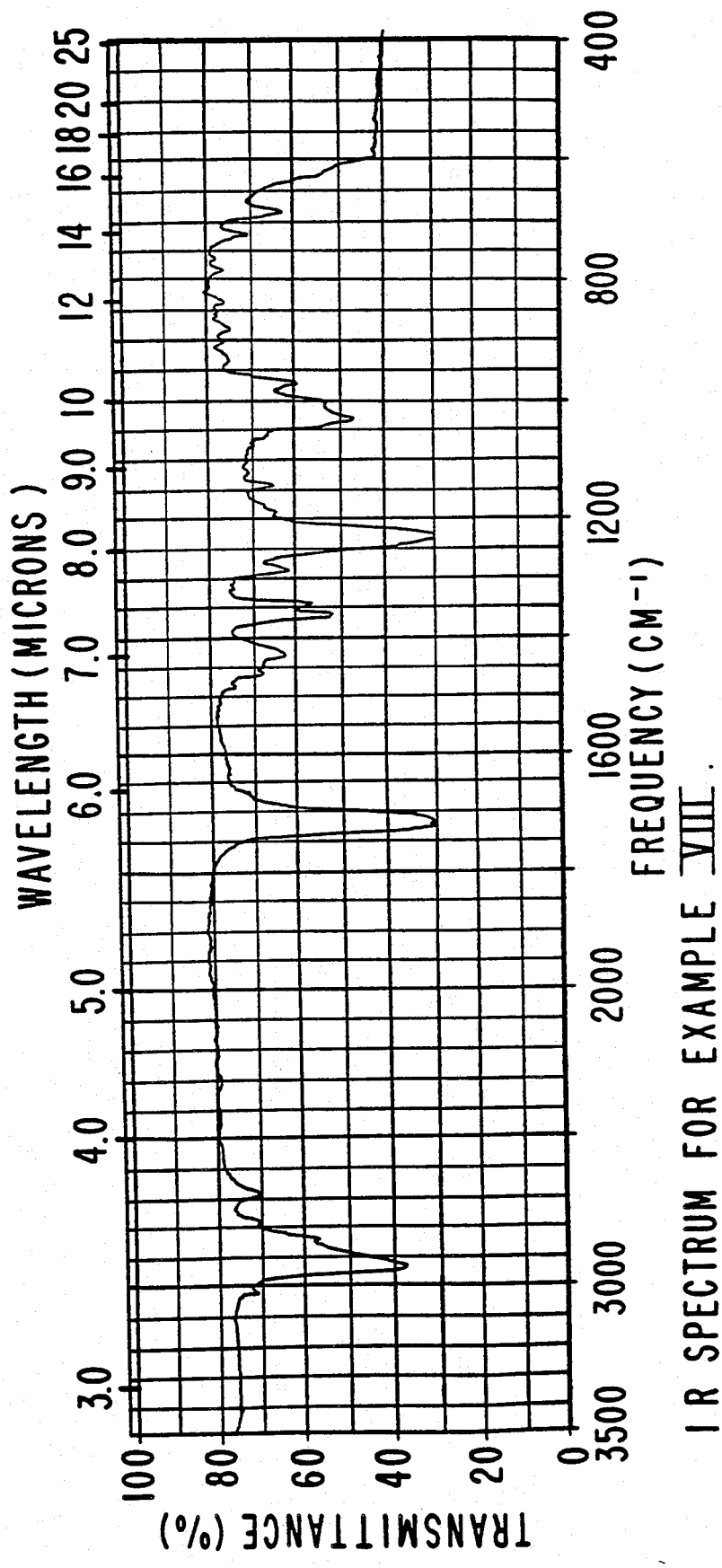

GLC PROFILE FOR EXAMPLE IX_CRUDE.

GLC PROFILE FOR FRACTION 9 OF EXAMPLE IX.

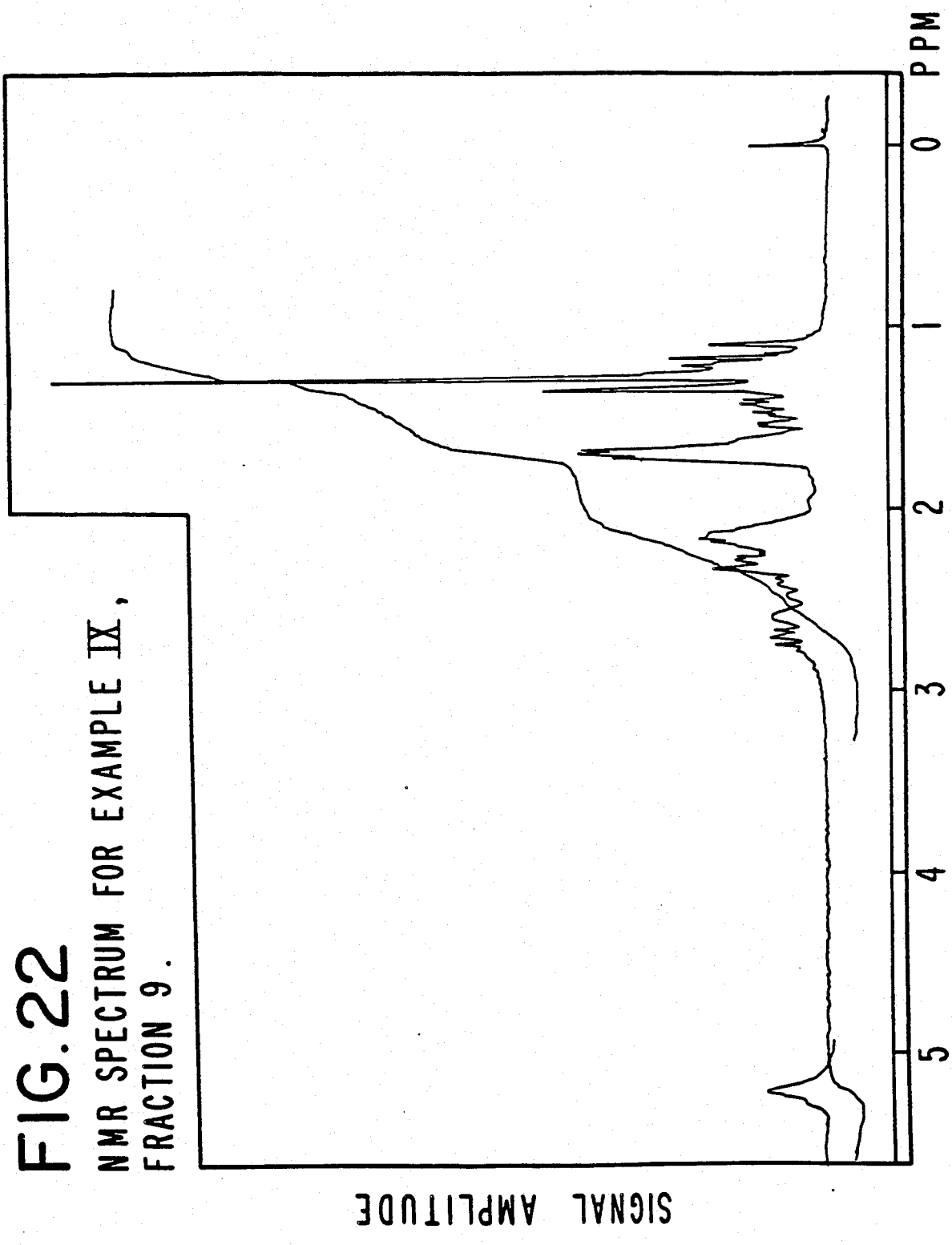
FIG. 22 NMR SPECTRUM FOR EXAMPLE IX, FRACTION 9.

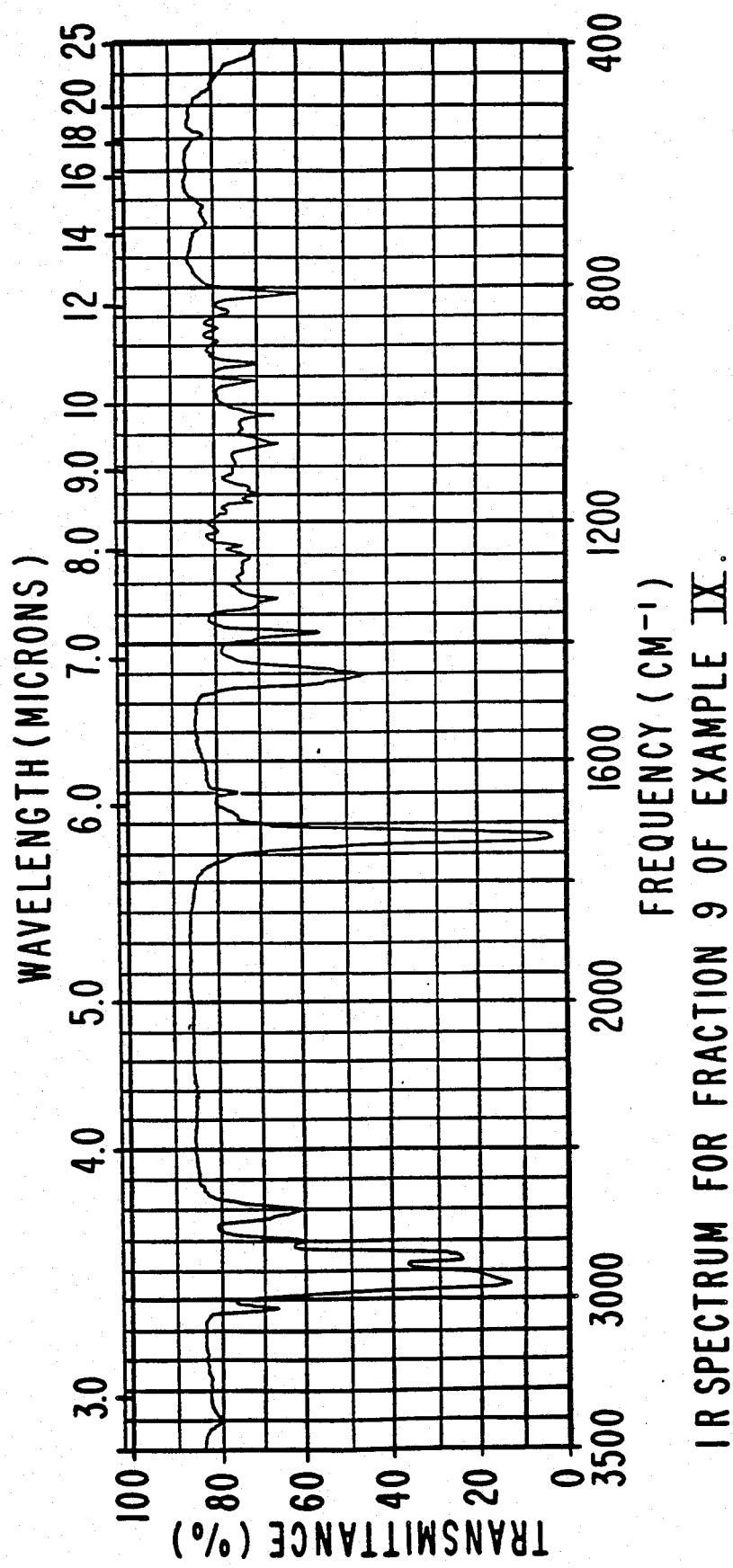

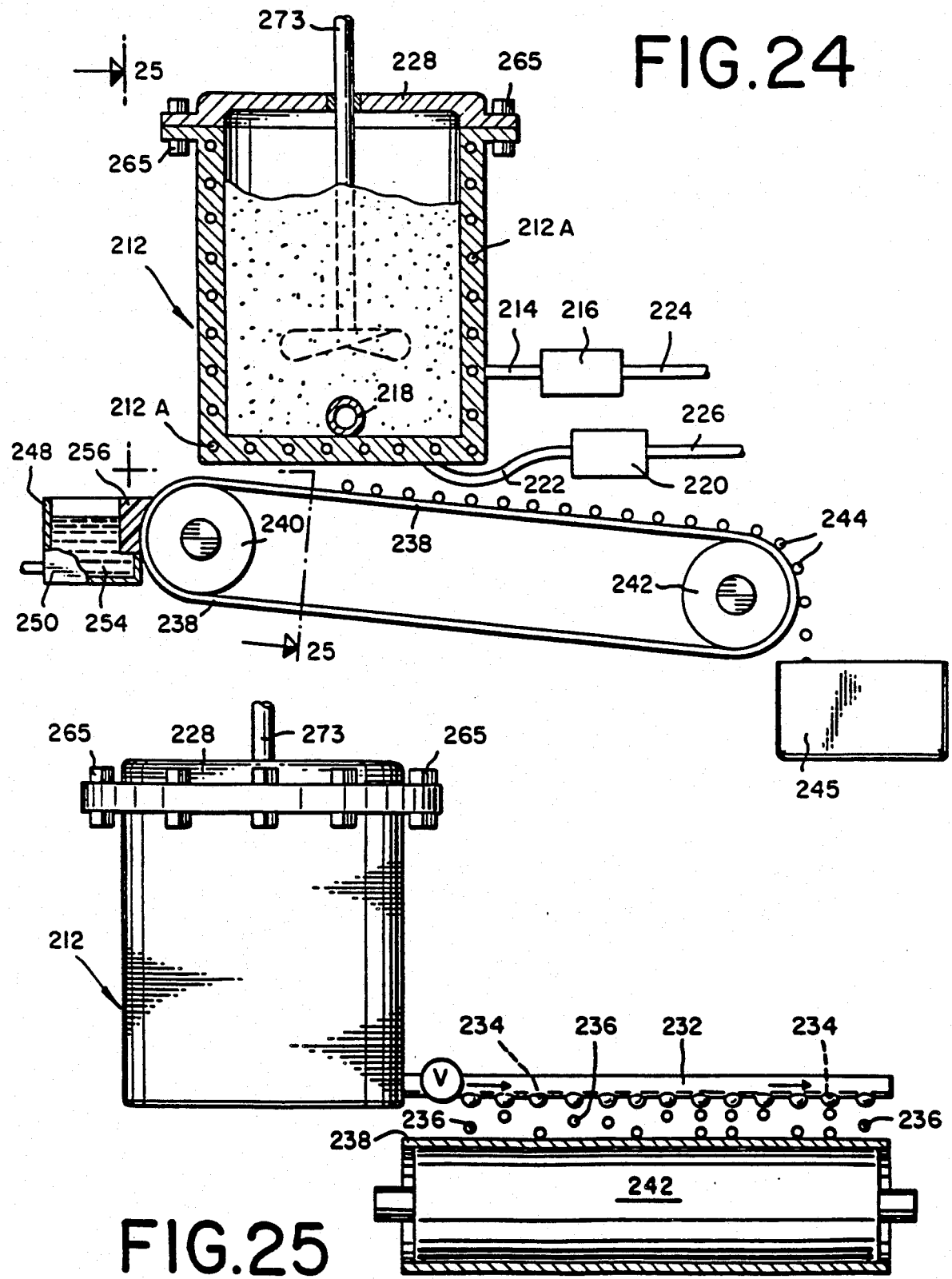

ALKOXY-SUBSTITUTED POLYHYDROINDAN CARBOXALDEHYDES

This is a divisional of application Ser. No. 712,164, filed Mar. 15, 1985 which, in turn, is a continuation-in-part of application for U.S. Letters Patent Ser. No. 528,568 filed Sept. 1, 1983 now U.S. Pat. No. 4,541,949 issued on Sept. 17, 1985.

BACKGROUND OF THE INVENTION

This invention relates to polyhydroindan carboxaldehydes and uses thereof in augmenting or enhancing the aroma of perfume compositions, perfumed articles and colognes.

Inexpensive chemical compositions of matter which can provide fresh, eucalyptus-like, balsamic, green, piney, ozoney, twiggy, woody and cinnamon-like aromas with green and twiggy, morning forest-like undertones are highly desirable in the art of perfumery. Many of the natural materials which provide such fragrances and contribute such desired nuances are high in cost, vary in quality from one batch to another and/or are generally subject to the usual variations of natural products.

In the course of the last twenty years particularly, an increasing amount of attention has been devoted to the preparation and utilization of artificial perfuming and odor modifying agents possessing the skeleton of tricyclo[5.2.1.0$_{2,6}$]decane. This attention has been stimulated mainly by an increased availability of cyclopentadiene, methylcyclopentadiene and the dimers thereof.

Thus, for example, U.S. Pat. No. 3,981,892 issued on Sept. 21, 1976 discloses the compounds defined according to the structure:

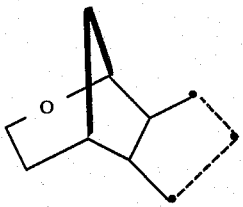

wherein one of the dashed lines represents a carbon-carbon double bond and the other of the dashed lines represents a carbon-carbon single bond for use in perfumery. German Pat. No. 1617021 shows the compounds defined according to the structure:

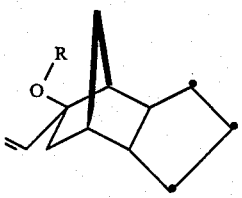

wherein R represents an acyl group or a hydrogen atom as possessing a perfuming note reminiscent of that developed by lavender oil. According to published Dutch Application No. 69/01750 the polycyclic gamma, delta-unsaturated aldehyde having the formula:

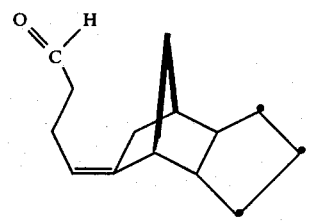

develops a green-fruity character which is reminiscent of the Lily of the Valley fragrance.

U.S. Pat. No. 3,446,755 issued on May 27, 1969 discloses perfume compositions relating to synthetic spike lavender oil which include as a key ingredient one or both of compounds defined according to the generic structure:

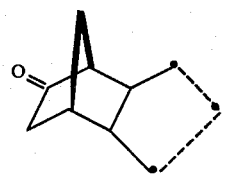

wherein one of the dashed lines represents a carbon-carbon double bond and the other of the dashed lines represent a carbon-carbon single bond.

The use of 4,7-methanoindene derivatives defined according to the structures:

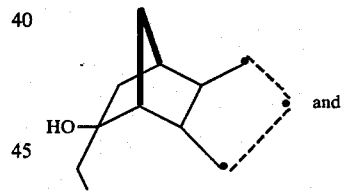

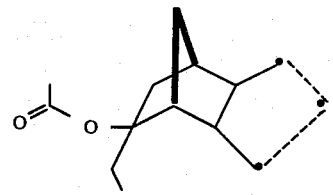

wherein one of the dashed lines in each of the molecules is a carbon-carbon double bond and the other of the dashed lines in each of the molecules is a carbon-carbon single bond is disclosed for use in perfumery (having odors which recall the odor of cardamon seed oil) in U.S. Pat. No. 3,417,132 issued on Dec. 17, 1968.

U.S. Pat. No. 4,275,251 issued on June 23, 1981 discloses the use of a genus of compounds defined according to the structure:

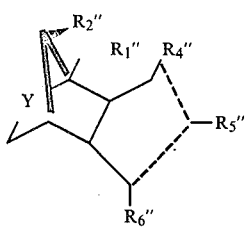

wherein one of $R_1''$ or $R_2''$ represents methyl and the other of $R_1''$ or $R_2''$ represents hydrogen; wherein one of $R_4''$ $R_5''$ and $R_6''$ represents methyl and the other of $R_4''$ $R_5''$ and $R_6''$ represent hydrogen; wherein Y represents one of the moieties:

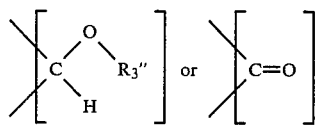

wherein $R_3''$ represents hydrogen, $C_1$-$C_3$ acyl; $C_3$-$C_4$ alkyl; $C_3$ or $C_4$ alkenyl or carbo-$C_1$-$C_3$ alkoxy for use in augmenting or enhancing the aroma of perfume compositions or perfumed articles.

Furthermore, other oxygenated compounds having a bicyclopentadiene nuclus are known in the prior art and uses in perfumery thereof are known. Thus, for example, Kheisets and Virezub at Chem. Abstracts, Volume 61: 8199c (abstract of Zh. Obshch. Khim. 34 (6) 2081-4) discloses for use in perfumery the compound defined according to the structure:

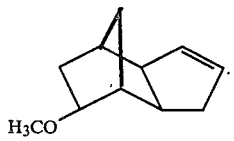

Zeinalov, et al at Chem. Abstracts 68, 49319d discloses the genus defined according to the structure:

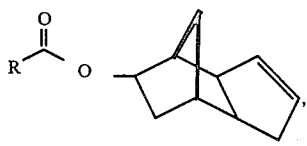

wherein R represents methyl, n-propyl or n-butyl.

Opdyke in Chem. Abstracts 92: 11070y (Abstract of Food, Cosmet. Toxicol. 1976, 14, Suppl. 889) discloses the compound having the structure:

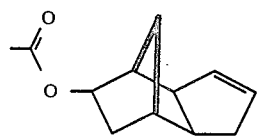

in fragrance raw materials as well as its toxicological properties.

The compound having the structure:

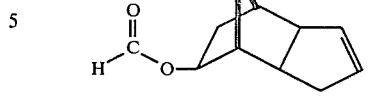

is disclosed in United Kingdom Patent specification No. 815,232 issued on June 24, 1959.

Furthermore, the compound having the structure:

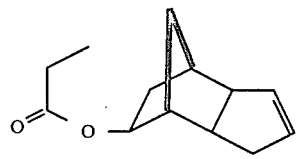

has been in use in the perfume industry for the past ten years and is known as "CYCLAPROP".

German Offenlengungsschrift No. 2,642,519 published on Mar. 23, 1978 and abstracted in Chem. Abstracts, 91: 56477g discloses for use in perfumery the compounds having the structures:

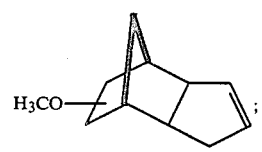

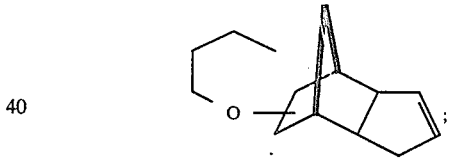

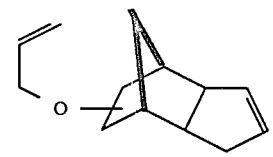

and the genus defined according to the structure:

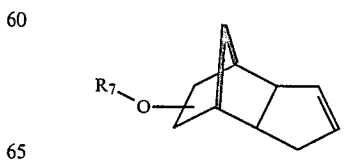

wherein $R_7$ is alkyl or alkenyl.

The genus defined according to the structure:

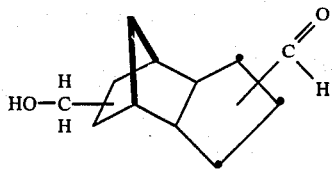

is disclosed at Chem. Abstracts, Volume 72: 21406p (Abstract of of South African Pat. No. 68/04722. The perfume use of the genus defined according to the structure:

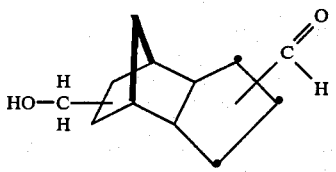

is set forth in Netherlands Published Application No. 76/08839 and German Offenlengungsschrift No. 2,623,285 published on Nov. 29, 1977. The genus defined according to the structure:

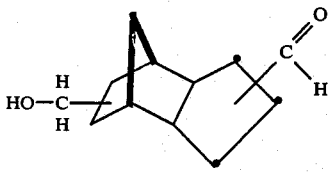

as indicated in Dutch Published Application No. 76/08839 to be produced by means of an oxo reaction of 2 moles of carbon monoxide and hydrogen on one mole of dicyclopentadiene followed by partial hydrogenation.

Other oxo reaction products produced useful in perfumery are disclosed, for example, in U.S. Pat. No. 3,985,769 issued on Oct. 12, 1976, for example, the compound defined according to the structure:

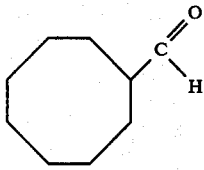

produced according to the reaction:

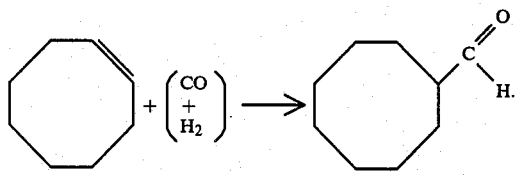

Nothing in the prior art however, discloses the polyhydroindan carboxaldehydes of our invention or mixtures of polyhydroindan carboxaldehydes of our invention or their organoleptic properties.

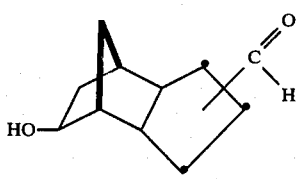

(Conditions: Field strength: 100 MHz; Solvent: CFCl$_3$).

Figure 2:
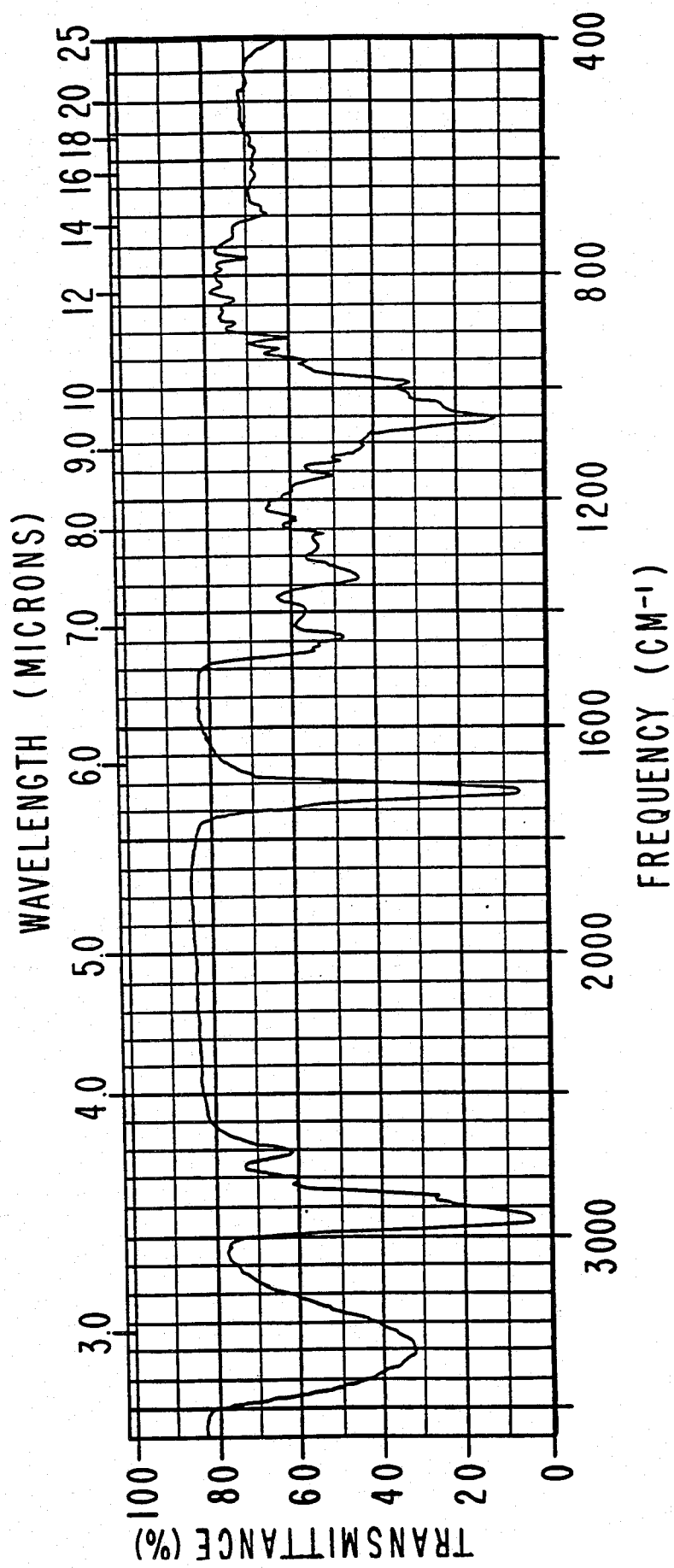

FIG. 2 is the infra-red spectrum for Fraction 4 of the distillation product of the reaction product of Example I containing a mixture of compounds defined according to the structure:

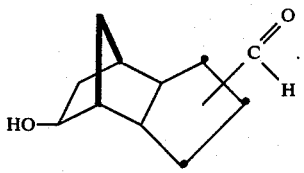

Figure 3:
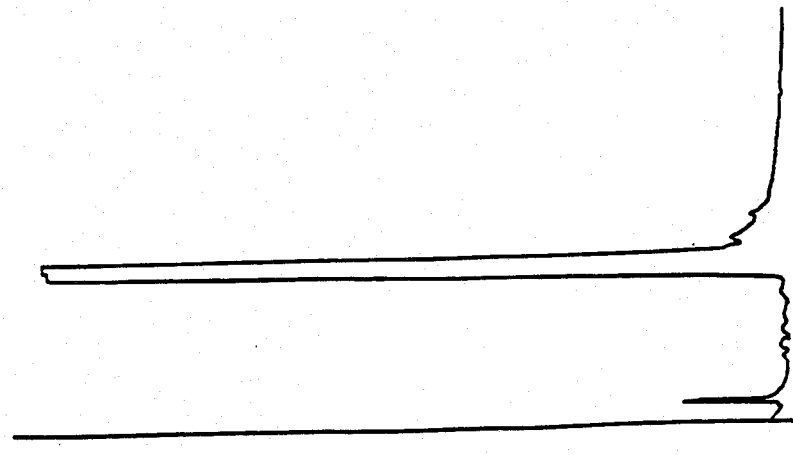

FIG. 3 is the GLC profile for the crude reaction product of Example II containing the compounds having the structures:

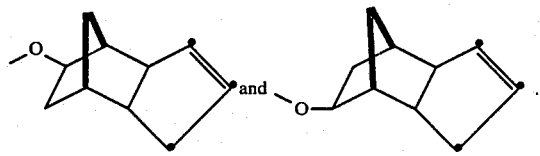

Figure 4:
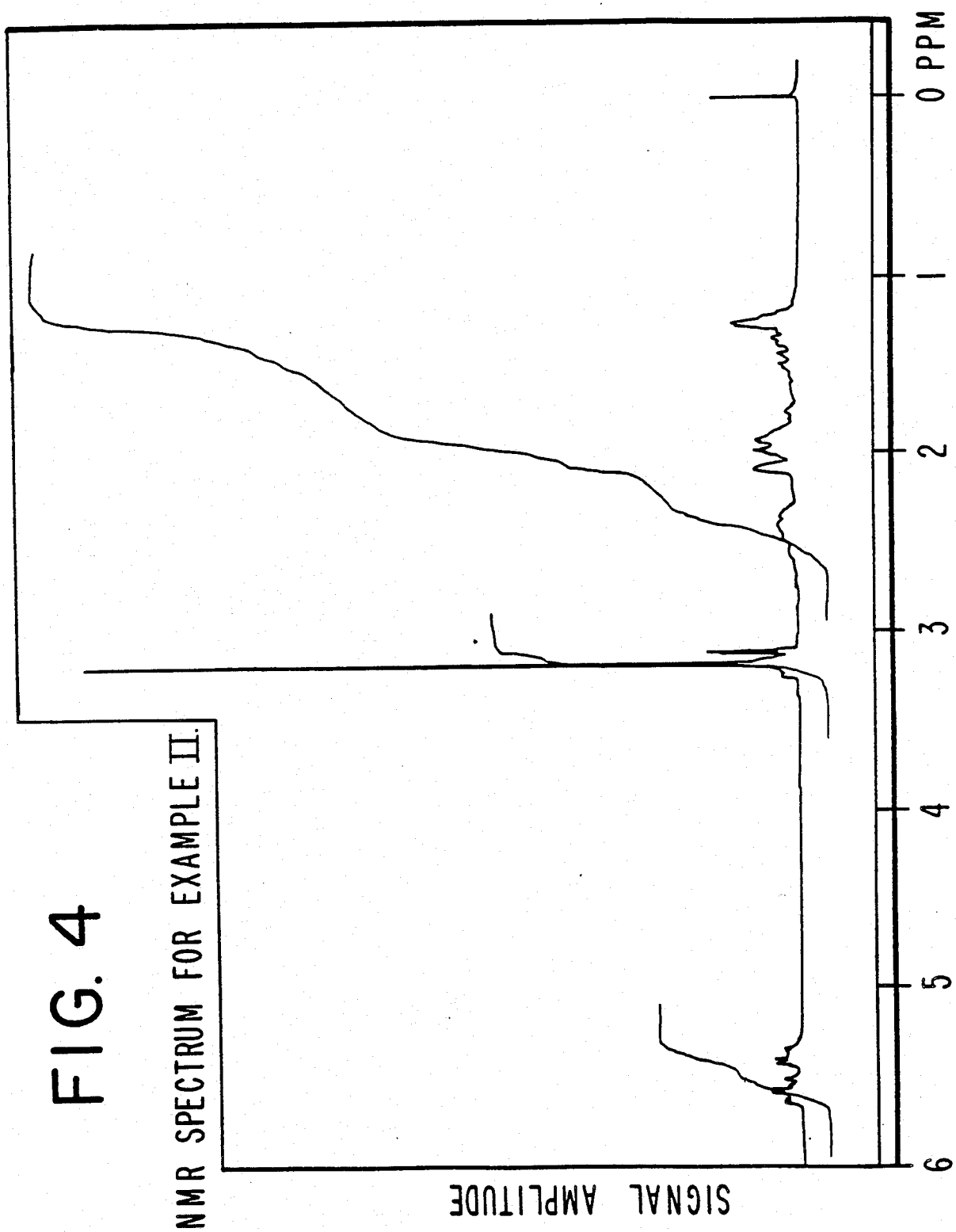

FIG. 4 is the NMR spectrum for the reaction product of Example II containing the compounds having the structures:

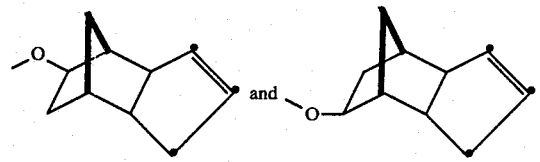

(conditions: Field strength: 100 MHz; Solvent: CFCl$_3$).

Figure 5:
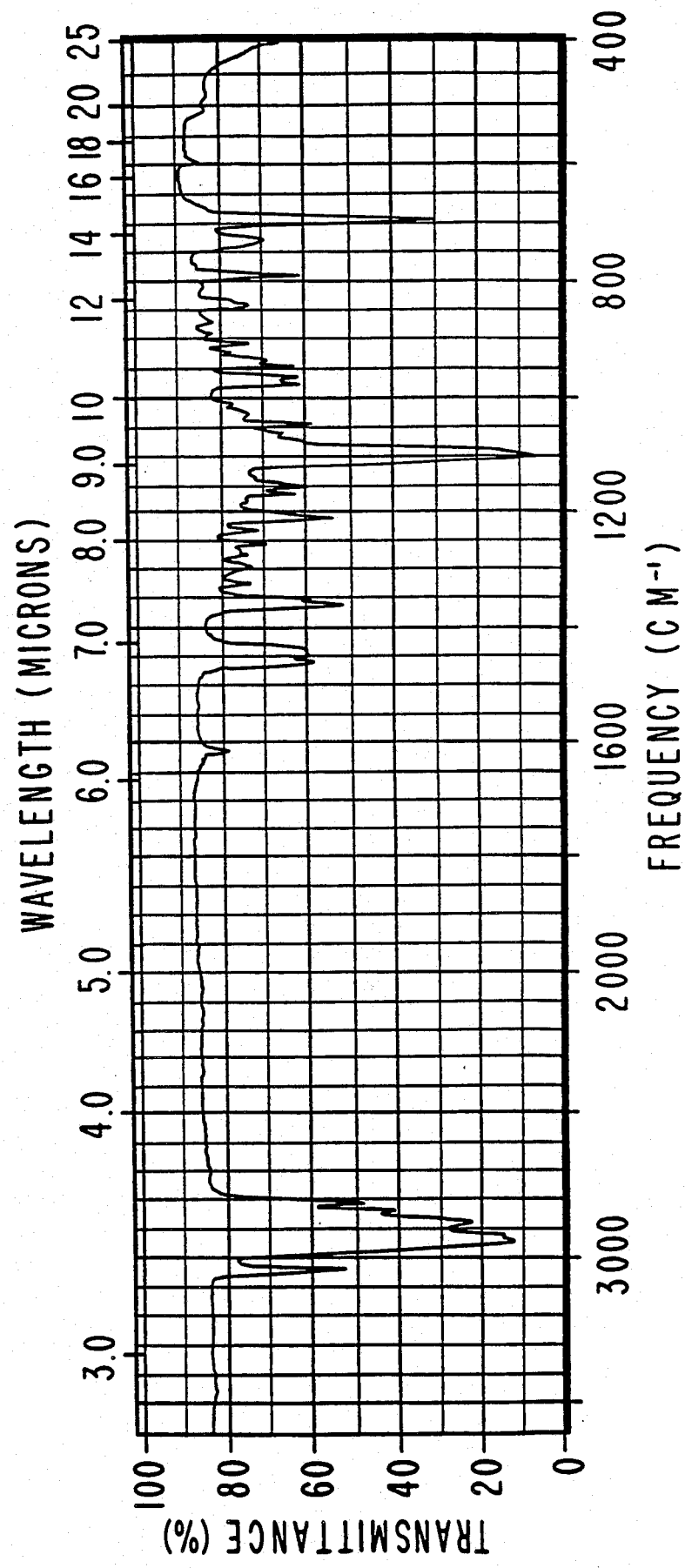

FIG. 5 is the infra-red spectrum for the reaction product of Example II containing the compounds having the structures:

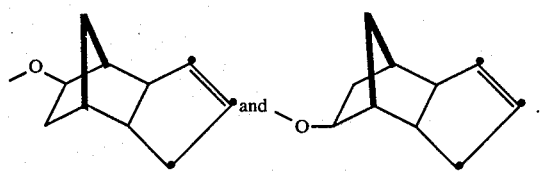

Figure 6:
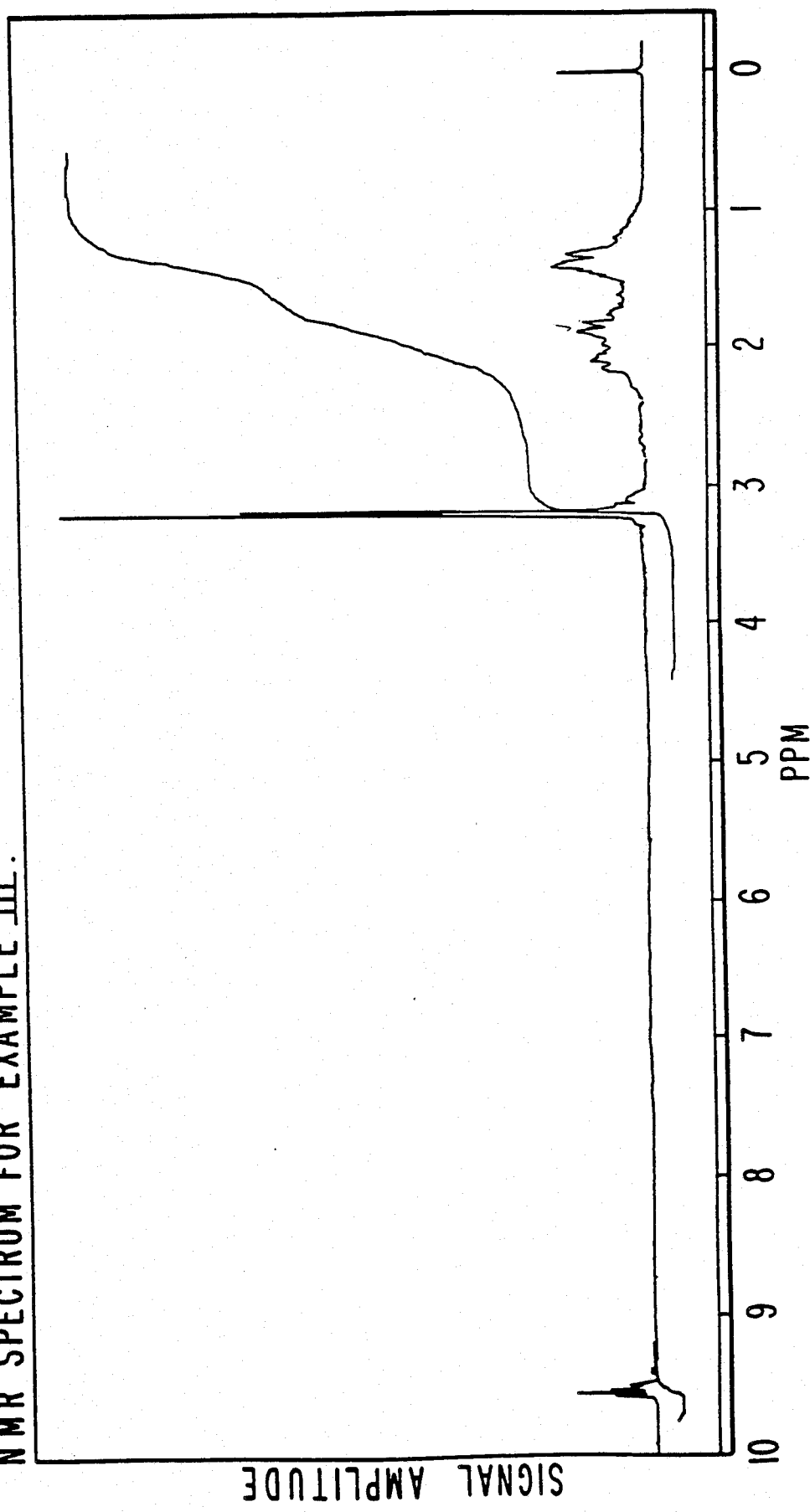

FIG. 6 is the NMR spectrum for the reaction product of Example III containing the compounds defined according to the structure:

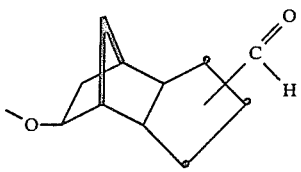

(conditions: Field strength: 100 MHz; Solvent: CFCl₃).

Figure 7:
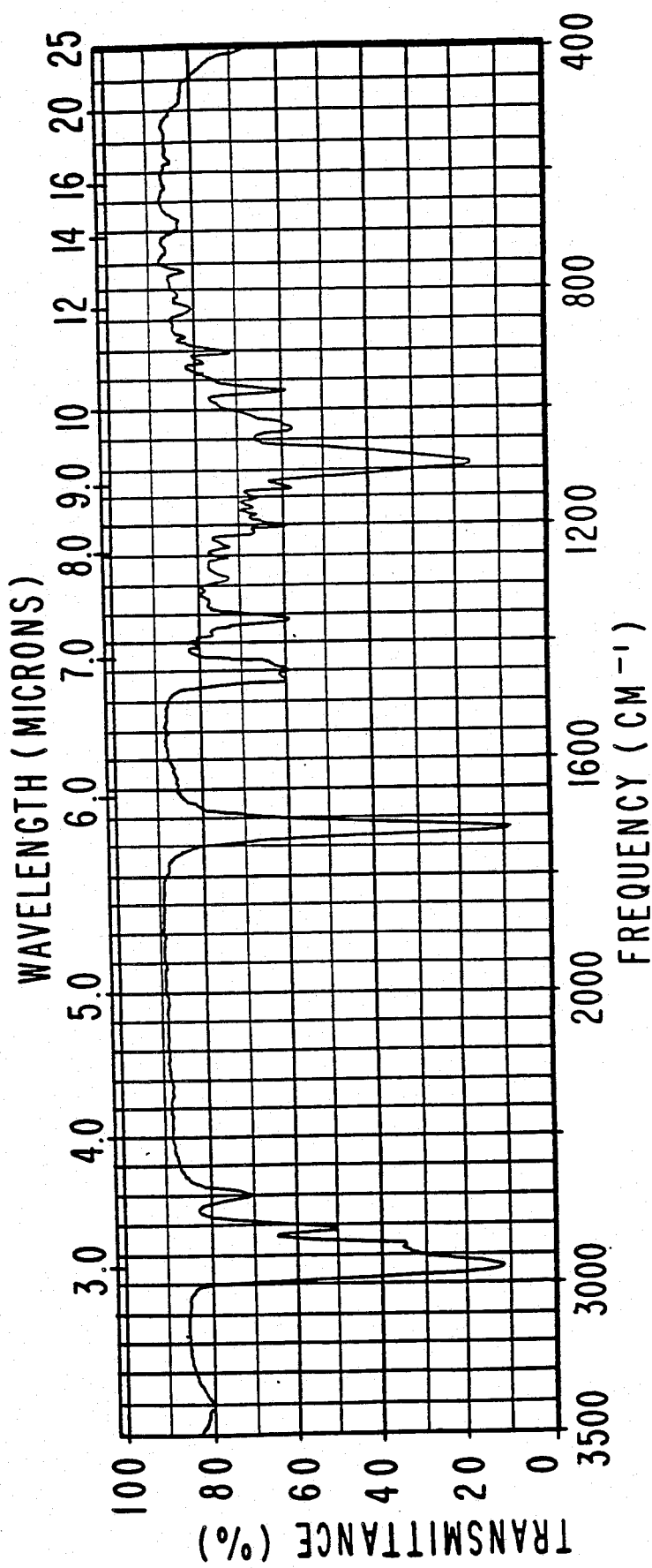

FIG. 7 is the infra-red spectrum for the reaction product of Example III containing the compounds defined according to the structure:

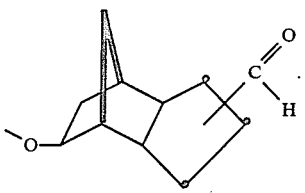

Figure 8:
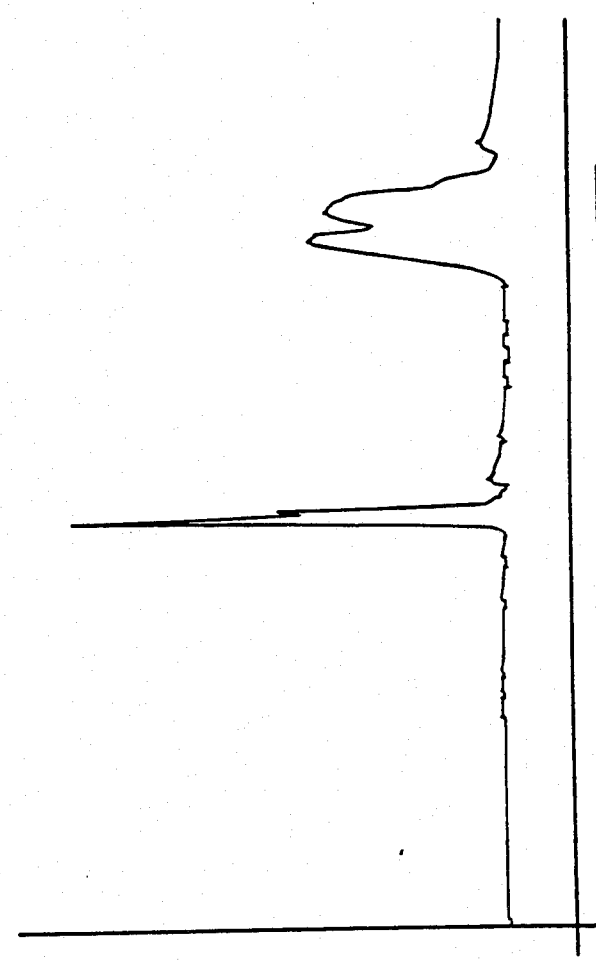

FIG. 8 is the GLC profile for the crude reaction product of Example IV containing the compounds defined according to the structure:

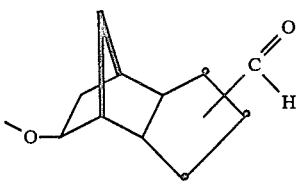

Figure 9:
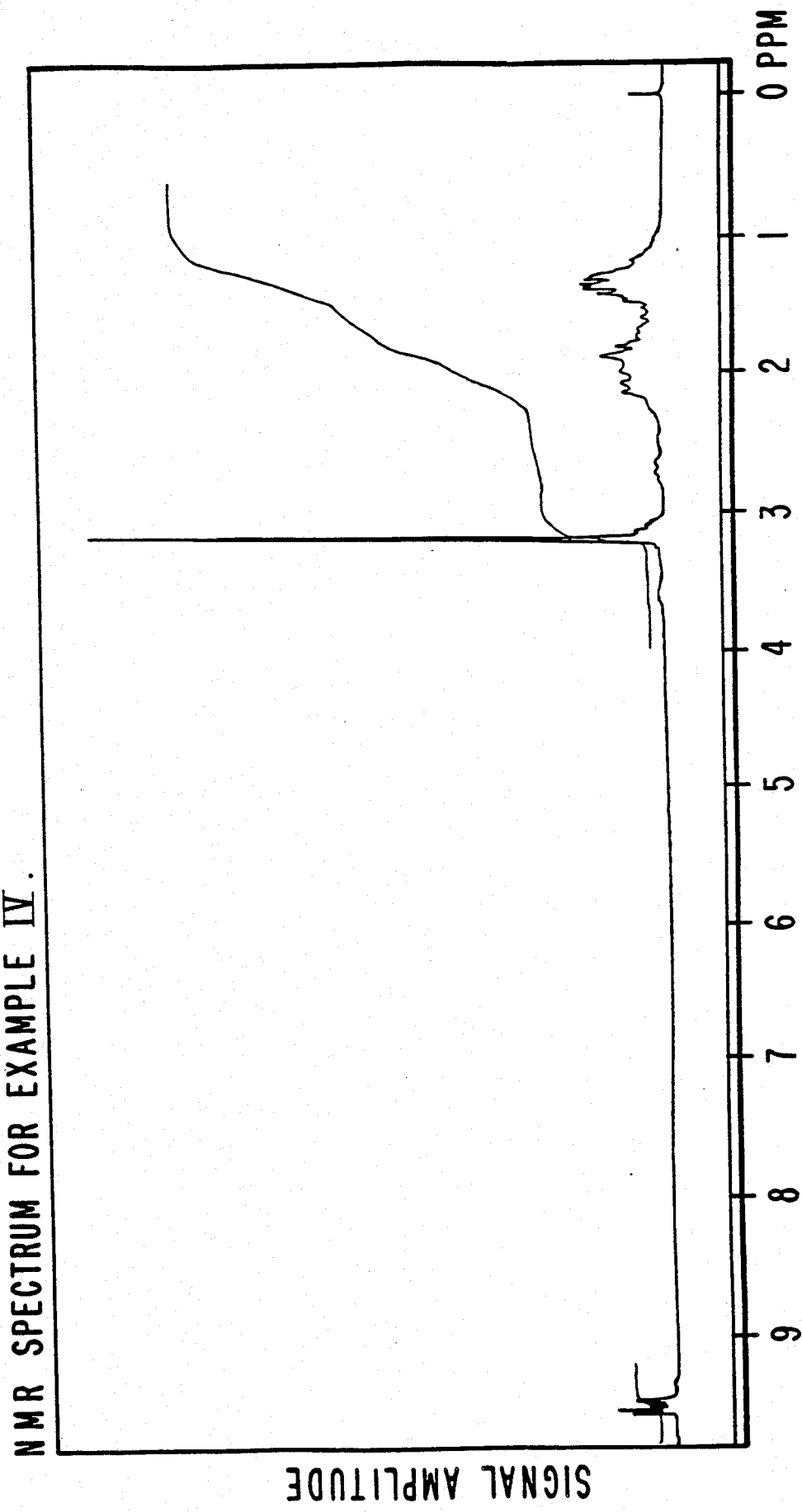

FIG. 9 is the NMR spectrum for the reaction product of Example IV containing the compounds defined according to the structure:

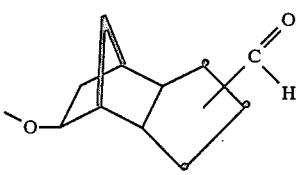

(conditions: Field strength: 100 MHz; Solvent: CFCl₃).

FIG. 10 is the infra-red spectrum for the first distillation Fraction 8 of the reaction product of Example IV containing the compounds having the structure:

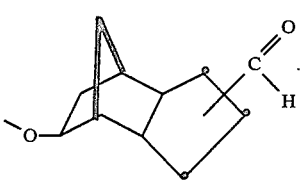

Figure 11:
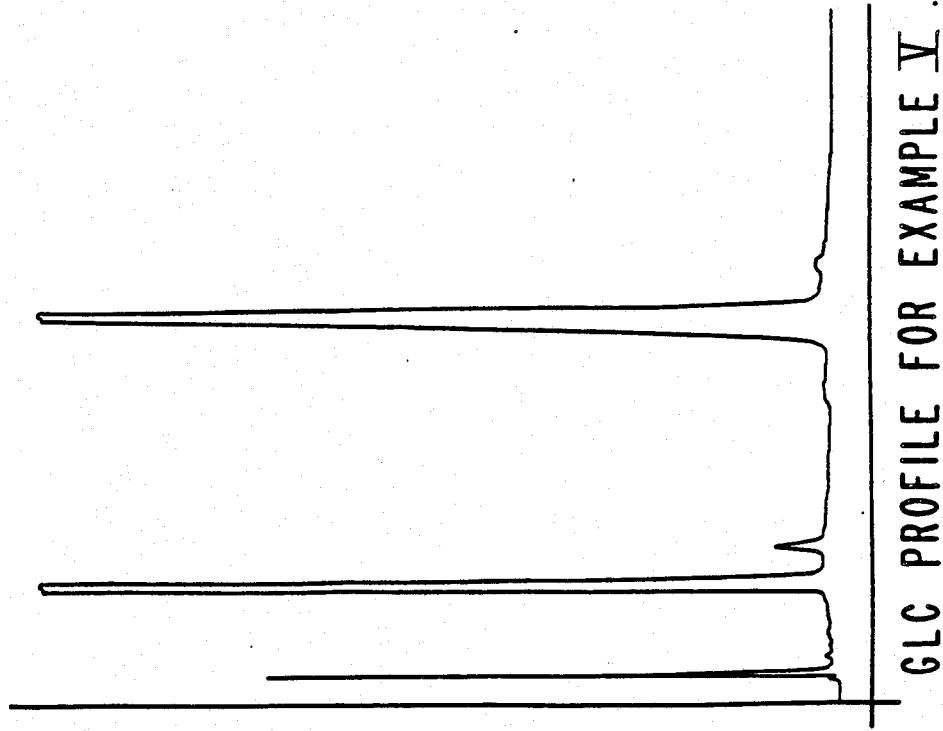

FIG. 11 is the GLC profile for the crude reaction product of Example V containing the compounds defined according to the structure:

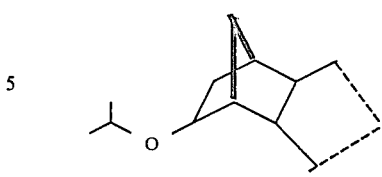

wherein the mixture in each of the molecules one of the dashed lines is a carbon-carbon double bond and the other of the dashed lines is a carbon-carbon single bond.

Figure 12:
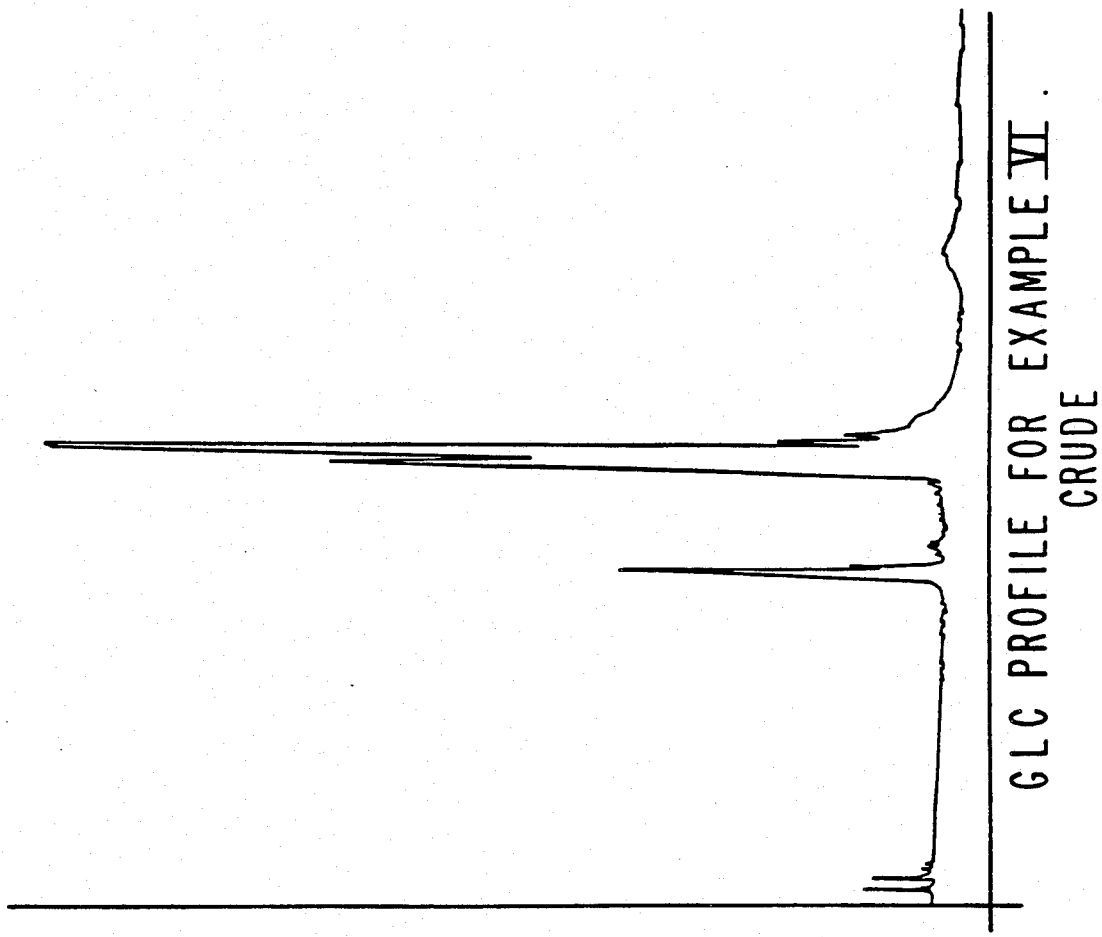

FIG. 12 is the GLC profile for the crude reaction product of Example VI containing the compounds defined according to the structure:

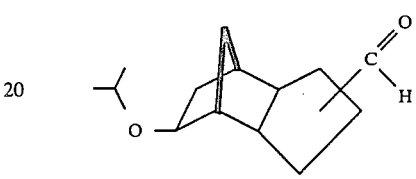

(Conditions: SE-30 column programmed at 80°–220° C. at 10° C. per minute).

FIG. 13 is the NMR spectrum for Fraction 8 of the distillation product of the reaction product of Example VI containing the compounds defined according to the structure:

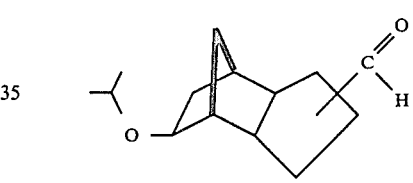

(Conditions: Field strength: 100 MHz; Solvent: CFCl₃).

FIG. 14 is the infra-red spectrum for Fraction 8 of the distillation product of the reaction product of Example VI containing the compounds defined according to the structure:

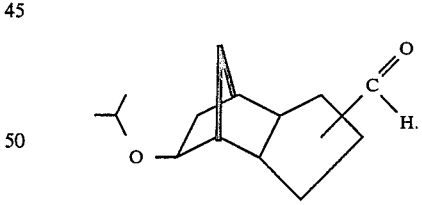

Figure 15:
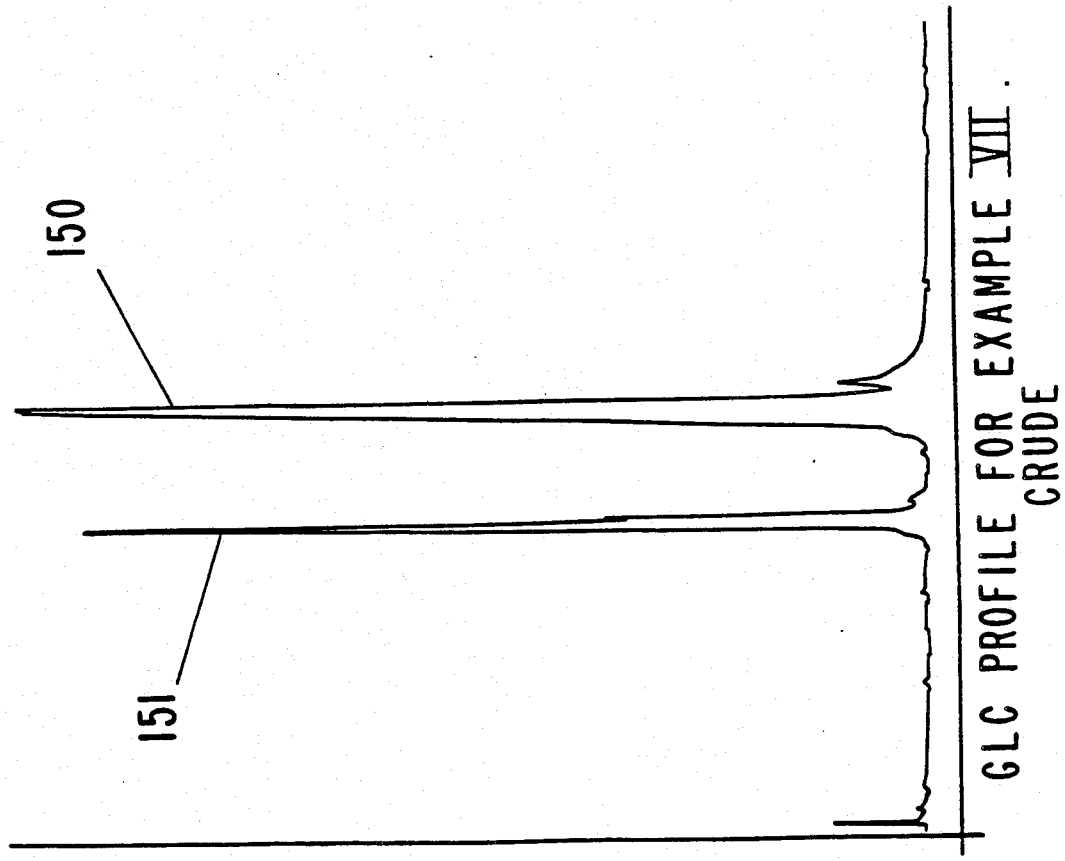

FIG. 15 is the GLC profile for the crude reaction product of Example VII containing the compounds defined according to the structure:

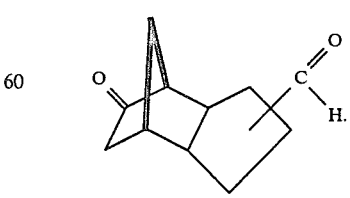

FIG. 16 is the NMR spectrum for the reaction product of Example VII containing the compounds defined according to the structure:

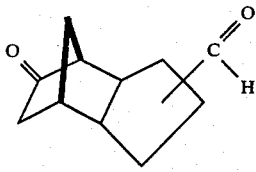

(Conditions: Field strength: 100 MHz; Solvent: CFCl₃).

FIG. 17 is the infra-red spectrum for Fraction 7 of the distillation product of the reaction product of Example VII containing the compounds defined according to the structure:

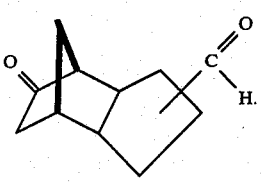

Figure 18:
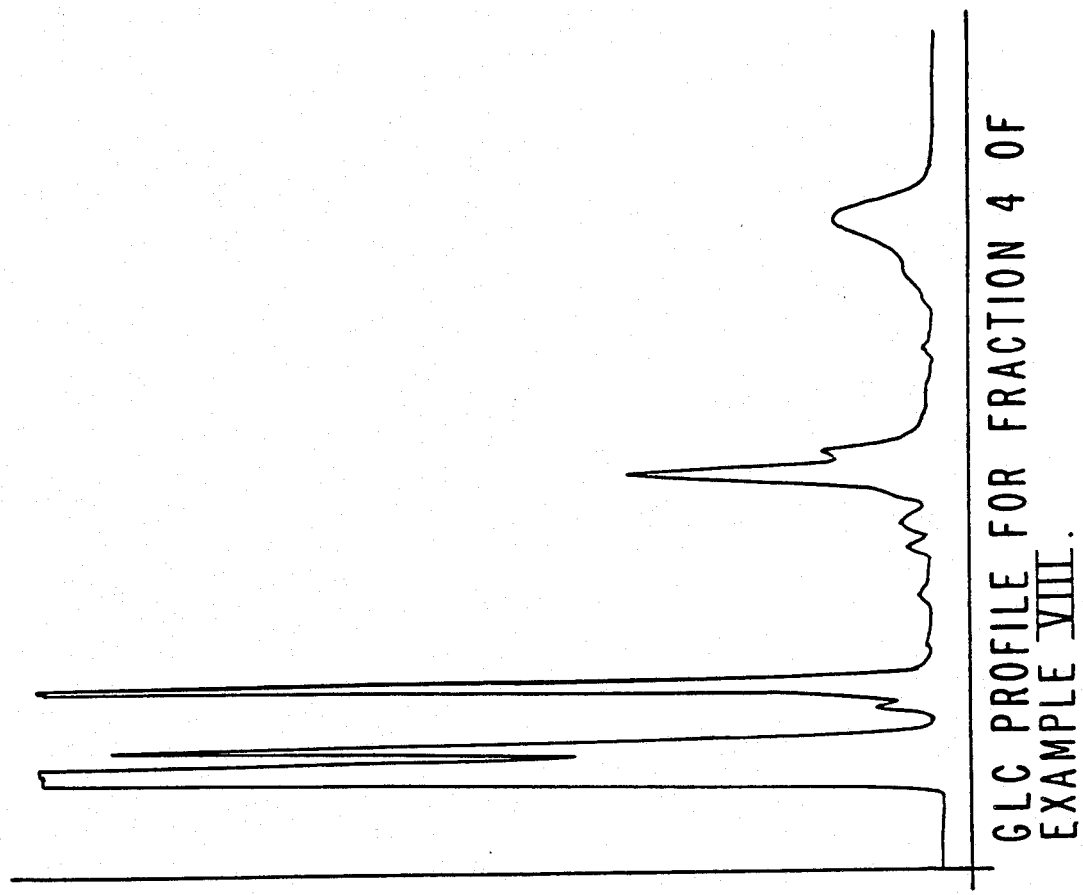

FIG. 18 is the GLC profile for Fraction 4 of the distillation product of the reaction product of Example VIII containing the compounds defined according to the structure:

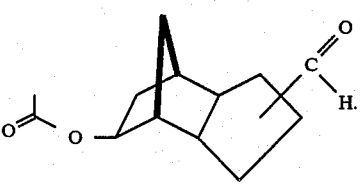

FIG. 19 is the infra-red spectrum for the reaction product of Example VIII containing the compounds having the structure:

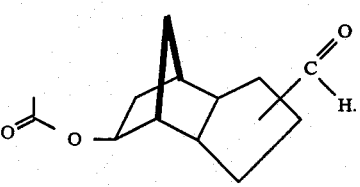

Figure 20:
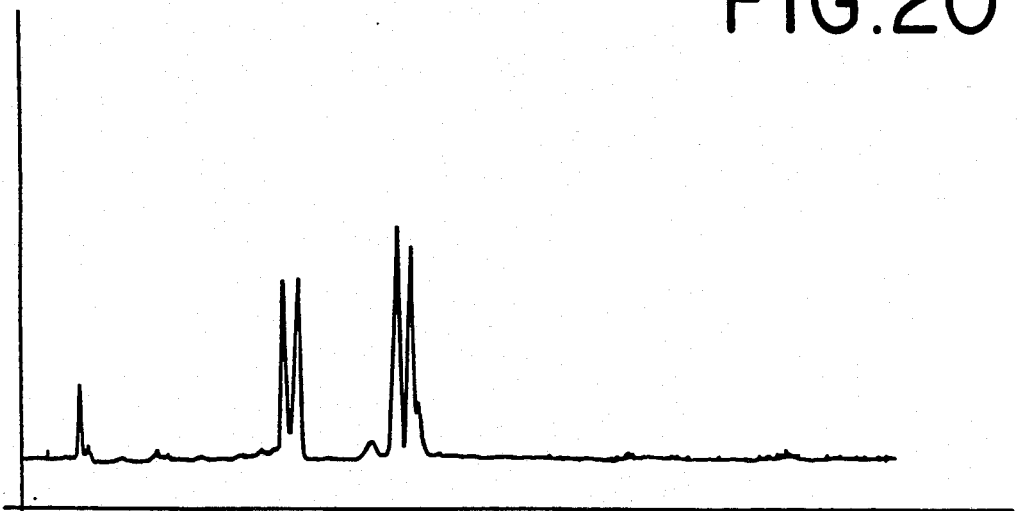

FIG. 20 is the GLC profile for the crude reaction product of Example IX containing the compounds having the structure:

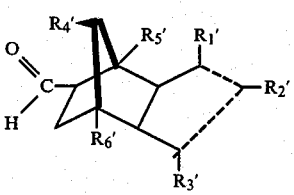

wherein a mixture is represented and in the mixture in each of the molecules at least one of the dashed lines is a carbon-carbon single bond, and when one of the dashed lines is a carbon-carbon single bond, the other of the dashed lines is a carbon-carbon double bond or a carbon-carbon single bond; wherein one of $R_4'$, $R_5'$, and $R_6'$ represents methyl and the other two of $R_4'$, $R_5'$, and $R_6'$ represents hydrogen; and wherein one of $R_1'$, $R_2'$, and $R_3'$ represents methyl and the other two of $R_1'$, $R_2'$ and $R_3'$ represents hydrogen.

Figure 21:
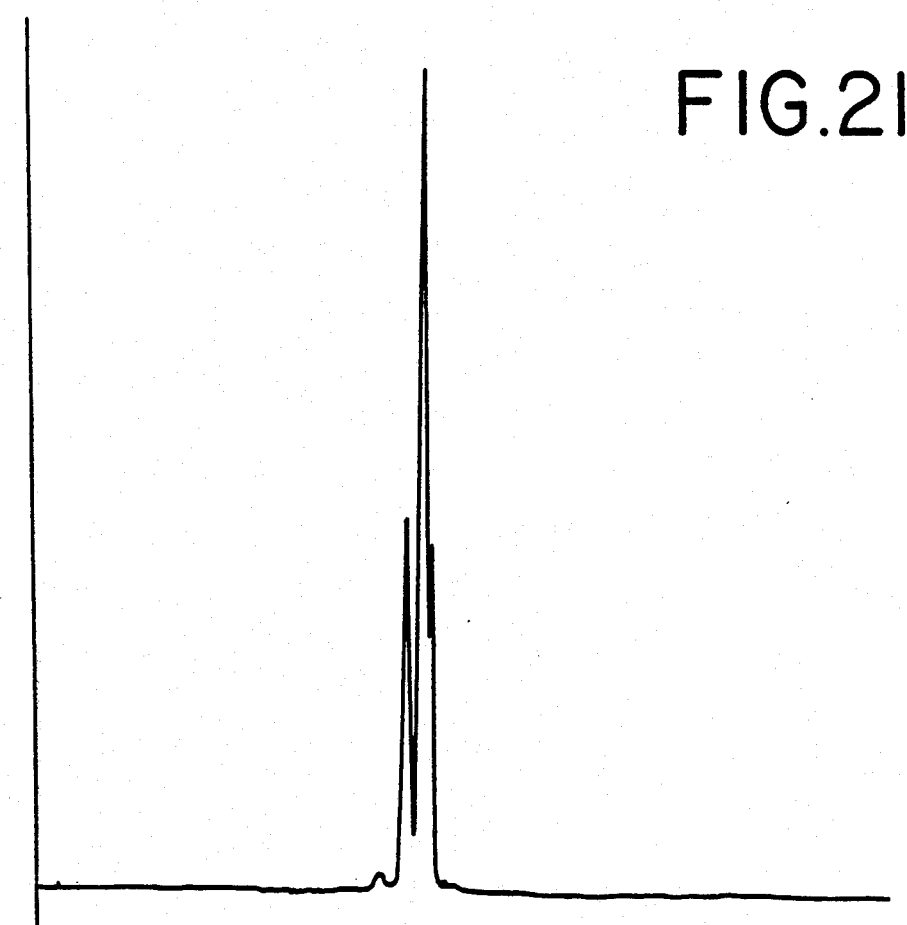

FIG. 21 is the GLC profile for Fraction IX of the distillation product of the reaction product containing a mixture of compounds defined according to the structure:

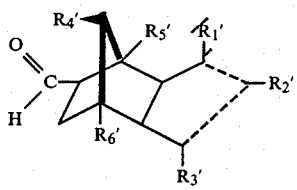

wherein a mixture is represented and in the mixture in each of the molecules at least one of the dashed lines is a carbon-carbon single bond, and when one of the dashed lines is a carbon-carbon single bond, the other of the dashed lines is a carbon-carbon double bond or a carbon-carbon single bond; wherein one of $R_4'$, $R_5'$, and $R_6'$ represents methyl and the other two of $R_4'$, $R_5'$, and $R_6'$ represents hydrogen; and wherein one of $R_1'$, $R_2'$, and $R_3'$ represents methyl and the other two of $R_1'$, $R_2'$ and $R_3'$ represents hydrogen;

(Conditions: Field strength: 100 MHz; Solvent: CFCl₃).

FIG. 23 is the infra-red spectrum for Fraction 9 of the distillation product of the reaction product of Example IX containing a mixture of compounds defined according to the structure:

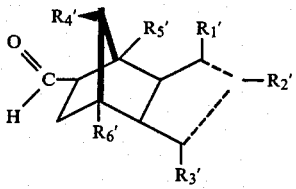

wherein a mixture is represented and in the mixture in each of the molecules at least one of the dashed lines is a carbon-carbon single bond, and when one of the dashed lines is a carbon-carbon single bond, the other of the dashed lines is a carbon-carbon double bond or a carbon-carbon single bond; wherein one of $R_4'$, $R_5'$, and $R_6'$ represents methyl and the other two of $R_4'$, $R_5'$, and $R_6'$ represents hydrogen; and wherein one of $R_1'$, $R_2'$, and $R_3'$ represents methyl and the other two of $R_1'$, $R_2'$ and $R_3'$ represents hydrogen.

FIG. 24 represents a cut-away side elevation view of apparatus used in forming perfumed polymers which contain imbedded therein at least one of the polyhydroindan carboxaldehydes of our invention.

FIG. 25 is a front view of the apparatus of FIG. 24 looking in the direction of the arrows.

DETAILED DESCRIPTION OF THE DRAWINGS

FIG. 15 is a GLC profile for the crude reaction product of Example VII (conditions: SE-30 column, programmed at 80°–220° C. at 10° C. per minute). The peak indicated by reference numeral "150" is the peak for the reaction product which is a mixture of compounds indicated by the structure:

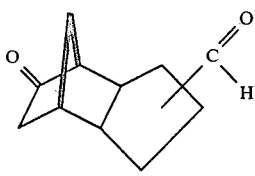

wherein the carboxaldehyde moiety in each of the molecules in the mixture is at any of three positions on the cyclopentano ring, to wit:

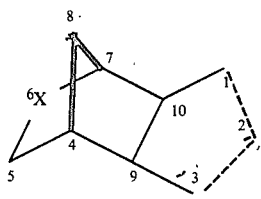

that is, the "1", the "2" or "3" positions. The peak indicated by reference numeral "151" is the peak for the starting material for the reaction of Example VII, that is, the composition of matter defined according to the structure:

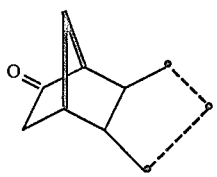

wherein one of the dashed lines represents a carbon-carbon double bond in each of the molecules of the mixture and the other of the dashed lines represents a carbon-carbon single bond in each of the molecules of the mixture.

Referring to FIGS. 24 and 25, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and, in addition, polyethylene) such as pellets useful in the formation of plastic particles, useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 24 and 25, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the polyhydroindan carboxaldehydes of our invention or mixtures of polyhydroindan carboxaldehydes and other compatible perfumes, is placed. The container is closed by means of an air-tight lid 228 and and clamped to the container by bolts 265. A stirrer 273 traverses the lid or cover 228 in an air-tight manner and is rotatable in a suitable manner. A surrounding cycliner 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the polyhydroindan carboxaldehydes of our invention is quickly added to the melt. Generally, about 10–45 percent by weight of the resulting mixture os the perfumery substance is added to the polymer.

After the perfume material is added to the container 212, the mixture is stirred for a few minutes, for example, 5–15 minutes, and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the polyhydroindan carboxaldehydes of our invention or mixture of perfume substance and one or more of the polyhydroindan carboxaldehydes of our invention, will continuously drop through the orifices of 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all of or which contains one or more of the polyhydroindan carboxaldehydes of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides compounds having the generic structure:

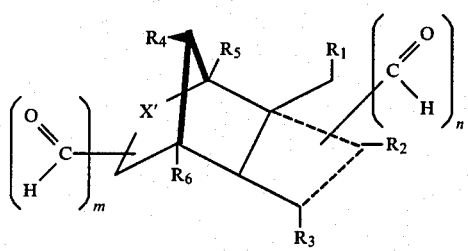

wherein each of the dashed lines represents a carbon-carbon single bond or a carbon-carbon double bond with the proviso that at least one of the dashed lines represents a carbon-carbon single bond; wherein one of $R_1$, $R_2$ and $R_3$ is hydrogen or methyl and each of the other of $R_1$, $R_2$ and $R_3$ represents hydrogen; wherein one of $R_4$, $R_5$ and $R_6$ represents hydrogen or methyl and each of the other of $R_4$, $R_5$ and $R_6$ represents hydrogen; wherein m is 0 or 1 and n is 0 or 1 and the sum of $m+n=1$; wherein X' represents one of the moieties:

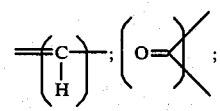

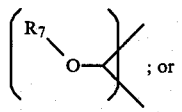

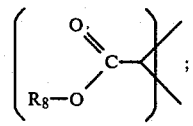

wherein $R_7$ represents $C_1$–$C_3$ alkyl or acetyl; and wherein $R_8$ represents $C_1$–$C_3$ alkyl with the proviso that when X' is methylene having the structure:

then m is 0 and n is 1 and with the further proviso that when m is 1, then one of the dashed lines represents a carbon-carbon double bond and one of $R_1$, $R_2$ and $R_3$ represents methyl and one of $R_4$, $R_5$ and $R_6$ represents methyl, and uses thereof in augmenting or enhancing the aroma of perfume compositions, colognes and perfumed articles (e.g., solid or liquid anionic, cationic, nonionic or zwitterionic detergents, fabric softener compositions, fabric softener articles, perfumed polymers and cosmetic powders). Also described is a process for preparing such polyhydroindan carboxaldehydes by reacting a tricyclic compound or mixture of compounds defined according to the structure:

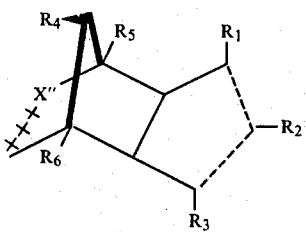

with carbon monoxide and hydrogen via an "oxo" reaction; wherein $R_1$, $R_2$, $R_3$, $R_4$ and $R_5$ are defined, supra; wherein one of the dashed lines represents a carbon-carbon single bond and the other of the dashed lines represents a carbon-carbon double bond; wherein X" represents one of the moieties:

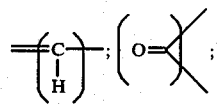

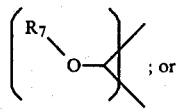

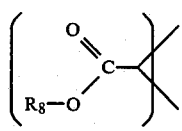

with the proviso that when X" is methylene having the structure:

then the line:

+ + + + + is a double bond and when X" is not methylene having the structure:

then the line:

+ + + + + is a carbon-carbon single bond.

The present invention also provides a process for preparing such compounds by means of carrying out an oxo reaction on compounds defined according to the structure:

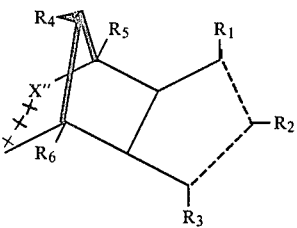

wherein $R_1$, $R_2$, $R_3$, $R_4$, $R_5$ and $R_6$ are as defined, supra; wherein $X''$ represents a moiety having the structures:

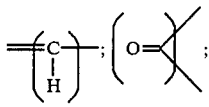

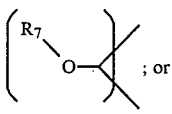

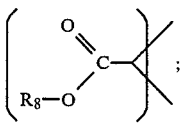

wherein $R_7$ represents $C_1$–$C_3$ alkyl; wherein $R_8$ represents $C_1$–$C_3$ alkyl; and wherein the line:

represents a carbon-carbon single bond or a carbon-carbon double bond with the proviso that the line:

is a carbon-carbon double bond when $X''$ is methylene hving the structure:

and wherein one of the dashed lines represents a carbon-carbon double bond and the other of the dashed lines represents a carbon-carbon single bond and the reaction being:

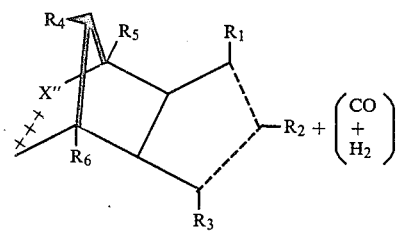

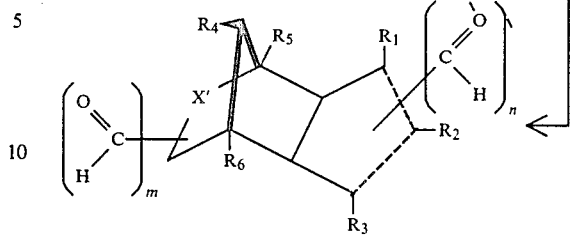

The present invention also provides products produced according to such process.

The resulting compounds, polyhydroindan carboxaldehydes of our invention produced according to the process of our invention, are capable of augmenting or enhancing the aromas of perfume compositions, colognes and perfumed articles (including soaps, anionic, cationic, nonionic or zwitterionic detergents, fabric softener compositions, optical brightener compositions, drier-added fabric softener articles and perfumed polymers) by imparting thereto or augmenting or enhancing fresh, eucalyptus, balsamic, green, piney, ozoney, twiggy, woody and cinnamon-like aroma nuances with green and twiggy undertones.

The polyhydroindan carboxaldehydes of our invention may be prepared by first preparing the precursor compounds of our invention defined according to the structure:

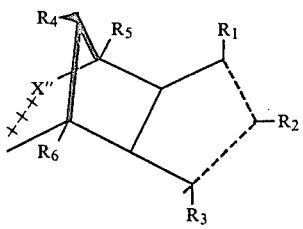

and then reacting such precursors with a mixture of carbon monoxide and hydrogen according to an oxo reaction to form the compounds defined according to the structure:

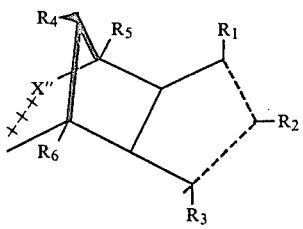

wherein $R_1$, $R_2$, $R_3$, $R_4$, $R_5$, $R_6$, $R_7$, $R_8$, n, m, $X'$, $X'''$, the dashed lines and the line:

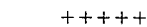

are defined, supra. Examples of the precursor compounds for carrying out our invention (insofar as their structures are concerned) are as follows:

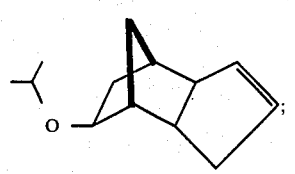

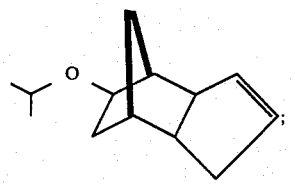

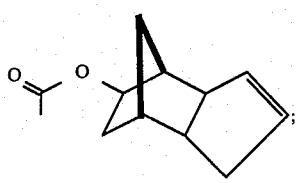

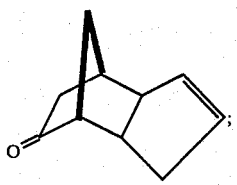

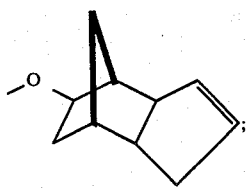

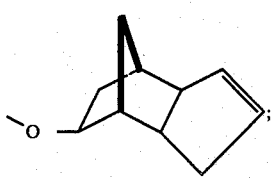

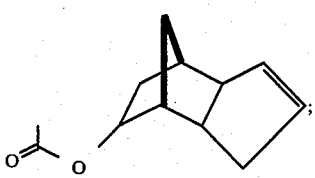

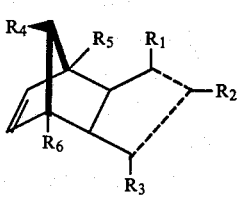

wherein one of $R_1$, $R_2$ and $R_3$ is methyl and the other of $R_1$, $R_2$ and $R_3$ is hydrogen; wherein one of $R_4$, $R_5$ and $R_6$ is methyl and the other of $R_4$, $R_5$ and $R_6$ are hydrogen; wherein one of the dashed lines is a carbon-carbon double bond and the other of the dashed lines represent carbon-carbon single bonds;

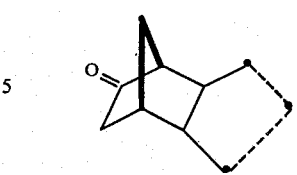

(mixture wherein one of the dashed lines is a carbon-carbon double bond and the other of the dashed lines is a carbon-carbon single bond);

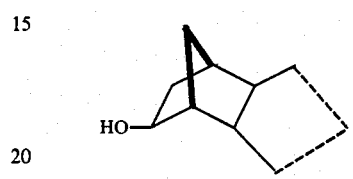

(mixture wherein one of the dashed lines is a carbon-carbon double bond and the other of the dashed lines is a carbon-carbon single bond);

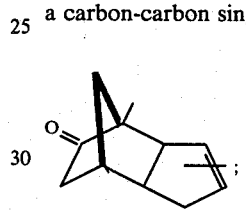

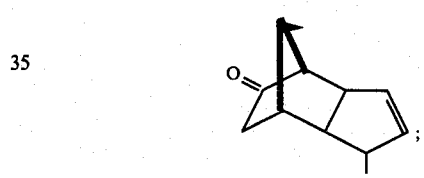

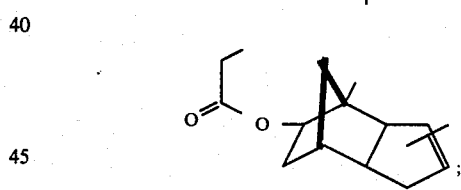

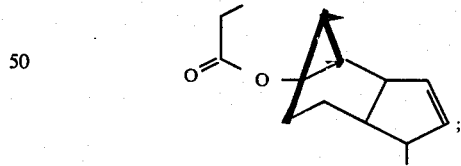

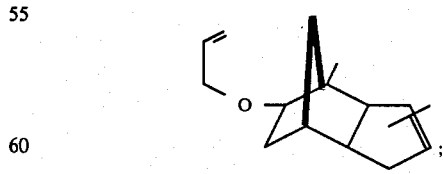

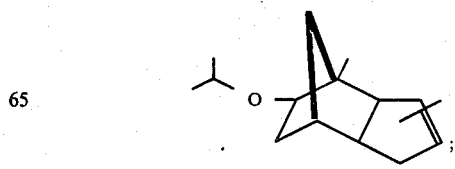

-continued
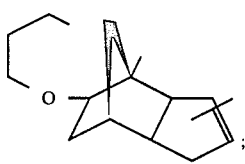
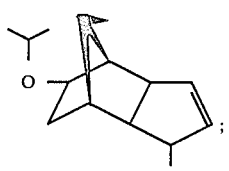
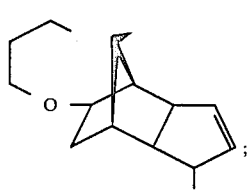
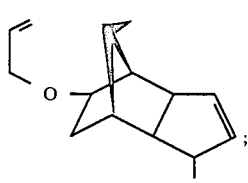
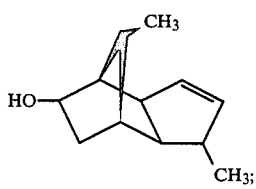
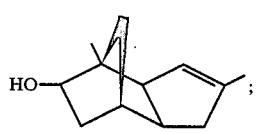
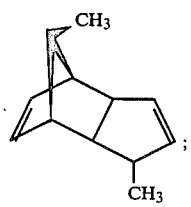
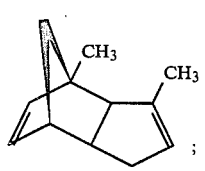
-continued
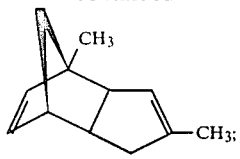
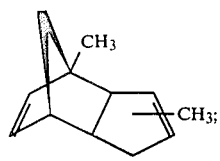
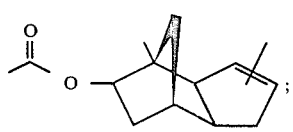
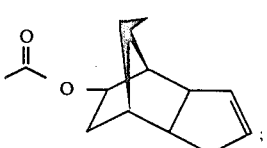
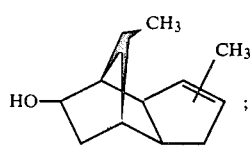
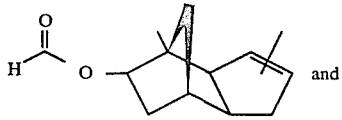 and
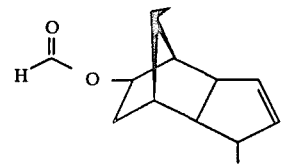
The foregoing reactants may be prepared according to procedures specifically exemplified in U.S. Pat. No. 4,275,251 issued in June 23, 1981 (the specification for which is incorporated by reference herein).
The "oxo" reaction is carried out thusly:

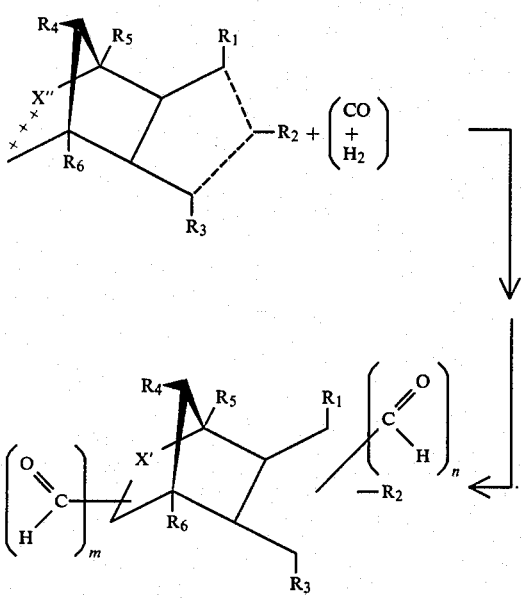

The reaction is carried out at temperatures of between 150° C. and 300° C.; at pressures of between 20 and 250 atmospheres; with the ratio of partial pressure of carbon monoxide:partial pressure of hydrogen being from 0.1:1 up to 1:0.1. Any oxo type reaction catalyst may be used, but most preferably, the reaction to yield the best perfume compositions are as follows:

Dicobalt octacarbonyl;
Cobalt octanoate;
Palladium chloride;
Rhodium trichloride;
Iron pentacarbonyl;
Nickel tetracarbonyl;
Polymer-bonded rhodium catalyst (e.g., rhodium bonded on a polystyrene substrate);
Tris-triphenyl phosphine rhodium-1-chloride;
Rhodium Acetoacetate dicarbonyl;
Rhodium Acetoacetate/triphenyl phosphine mixture.

The reaction time may vary from about 2 hours up to about 30 hours; and the reaction time is a function of the temperature and pressure of reaction. If the reaction is carrried out for too long a period of time, the aldehyde product is converted in a large proportion to alcohols. Insofar as the instant invention is concerned, it is most desirable to have substantially all aldehyde in the reaction product. High temperature, high pressure and too long a period of time of reaction will create too high a ratio of alcohol:aldehyde reaction product. Accordingly, it is most advisable to stay within the limits set forth, supra for the purposes of this invention.

At the end of the reaction the reaction product is separated from the catalyst and unreacted materials by standard "work-up" means; e.g., neutralization of catalyst; followed by extraction and fractional distillation; usually an initial fractional distillation by means of distillation through a 2, 3, or 4 plate or stone packed column; followed by a more careful fractionation of the bulked center-cut fractions on, for example, a spinning band column or multiplate (10–50 plate) fractionation column.

Examples of polyhydroindan carboxaldehydes which are useful in the practice of our invention and examples of dicyclopentadiene reactants, and the organoleptic properties of the polyhydroindan carboxaldehydes which are useful in the practice of our invention are set forth in the following Table I:

TABLE I

| Bicyclopentadiene Reactant | Oxo Reaction Product | Perfumery Properties |
|---|---|---|
| (structure shown) | (structure shown) | A floral woody aroma profile. |
| (A mixture wherein in the mixture one of the dashed lines is a carbon-carbon double bond and the other of the dashed lines is a carbon-carbon single bond). | | |
| (structure shown with $R_7$, $R_5$, $R_1$, $R_2$, $R_6$, $R_3$) | (structure shown with $R_7'$, $R_5'$, $R_1'$, $R_2'$, $R_6'$, $R_3'$) | A fresh, eucalyptus balsamic and green aroma profile. |
| (A mixture wherein in the mixture in each of the molecules one of the dashed lines is a carbon-carbon double bond and the other of the dashed lines is a carbon-carbon single bond; wherein one of $R_1$, $R_2$ and $R_3$ is methyl and the other of $R_1$, $R_2$ and $R_3$ are hydrogen; wherein one of $R_4$, $R_5$ and $R_6$ is | (A mixture wherein in the mixture one of the dashed lines is a carbon-carbon double bond and the other of the dashed lines is a carbon-carbon single bond; wherein one of $R_1'$, $R_2'$ and $R_3'$ in each of the molecules of the mixture is methyl and the other of $R_1'$, $R_2'$ and $R_3'$ is hydrogen; wherein in the mixture one of $R_4'$, $R_5'$ and $R_6'$ is methyl and the other | |

TABLE I-continued

| Bicyclopentadiene Reactant | Oxo Reaction Product | Perfumery Properties |
|---|---|---|
| methyl and the other of R₄, R₅ and R₆ is hydrogen). | of R₄', R₅' and R₆' is hydrogen). | |
| (structure with -O- substituent) (A mixture wherein in the mixture in each of the molecules one of the dashed lines is a carbon-carbon double bond and the other of the dashed lines is a carbon-carbon single bond) | (structure with -O- and CHO substituents) | A woody, piney, green and ozoney aroma with green and twiggy undertones. |
| (isopropoxy structure) (A mixture wherein in the mixture one of the dashed lines is a carbon-carbon double bond and the other of the dashed lines is a carbon-carbon single bond) | (isopropoxy structure with CHO) | A twiggy, green and ozoney arpma with woody and green undertones. |
| (ketone structure) (A mixture wherein in the mixture in each of the molecules one of the dashed lines is a carbon-carbon double bond and the other of the dashed lines is a carbon-carbon single bond) | (ketone structure with CHO) | A cinnamon-like and green aroma with green and woody undertones. |

In U.S. Pat. No. 4,390,717 a mono carboxcyclic acid ester of dicyclopentadiene is formed by reacting dicyclopentadiene with carbon monoxide at a pressure of at least 30 kg/cm² and an alcohol in the presence of a cobalt compound catalyst. The process is characterized by carrying out the reaction at a temperature of 130° C. or less in the presence of a pyridine base in an amount of 0.5 mole or more per mole of dicyclopentadiene to hydroesterify the double bond of the norbornene ring in accordance with the following reaction:

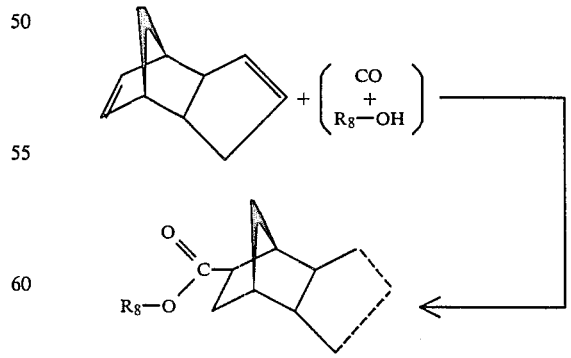

wherein R₈ is lower alkyl.

The resulting compound defined according to the structure:

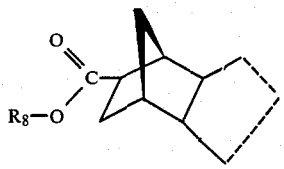

may then be reacted with a mixture of carbon monoxide and hydrogen by means of an "oxo" reaction whereby a carboxaldehyde moiety will be bonded to one of the carbon atoms previously bonded via carbon-carbon double bond to another carbon atom in the cyclopentanone ring according to the reaction:

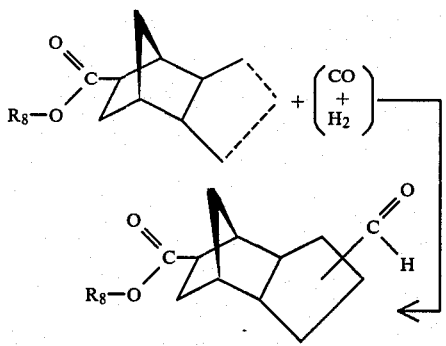

wherein in the molecules having dashed lines (showing a mixture) in the mixture one of the dashed lines is a carbon-carbon double bond and the other of the dashed lines is a carbon-carbon single bond.

The resulting compounds defined according to the structure:

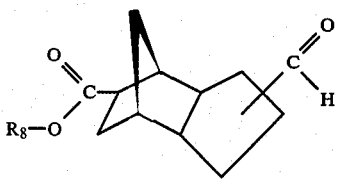

is a mixture of carboxaldehyde derivatives.

One of more the polyhydroindan carboxaldehydes prepared in accordance with the process of our invention and one or more auxiliary perfume ingredients including, for example, alcohols, aldehydes other than the polyhydroindan carboxaldehydes of our invention, ketones, terpenic hydrocarbons, nitriles, esters, lactones, natural essential oils, synthetic essential oils, mercaptans and alkyl mercapto derivatives may be admixed so that the combined odors of the individual components produce a pleasant and desired fragrance, particularly and preferably in woody, pine, floral and eucalyptus type fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients. Thus, one or more of the polyhydroindan carboxaldehydes of our invention can be used to alter, modify or enhance the aroma characteristics of a perfume composition, for example, by utilizing or moderating the olfactory reaction contributed by another ingredient in the composition.

The amount of one or more of the polyhydroindan carboxaldehydes of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing (agents) and colognes depends on many factors, including the other ingredients, their amounts and the effects which are desired. It has been found that perfume compositions containing as little as 0.01% of one or more of the polyhydroindan carboxaldehydes of our invention and less than 50% of one or more of the polyhydroindan carboxaldehydes or even less (e.g., 0.005%) can be used to impart a floral, woody, fresh, eucalyptus-like, balsamic, green, piney, twiggy, and cinnamon-like aromas with green, woody and twiggy undertones to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

One or more of the polyhydroindan carboxaldehydes of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers. When used as (an) olfactory component of a perfumed article as little as 0.2% of one or more of the polyhydroindan carboxaldehydes of our invention will suffice to impart an intense floral, woody, fresh, eucalyptus-like, balsamic, green, piney, ozoney and twiggy aroma profile with green, twiggy and woody undertones to floral, woody, eucalyptus-like or piney formulations. Generally, no more than 6% of one or more of polyhydroindan carboxaldehydes of our invention based on the ultimate end product is required in the perfumed article composition. Accordingly, the range of polyhydroindan carboxaldehydes in the perfumed article is from about 0.2% by weight of the polyhydroindan carboxaldehydes based on the perfumed article up to about 6% by weight based on the perfumed article. In addition, the perfume composition or fragrance composition of our invention can contain a vehicle or carrier for one or more of the polyhydroindan carboxaldehydes of our invention. The vehicle can be a liquid, such as a non-toxic alcohol, e.g, ethyl alcohol, a non-toxic glycol, e.g., propylene glycol or the like. The carrier can also be an absorbent solid, such as a gum (e.g.) gum arabic, guar gum or xanthan gum) or components for encapsulating the composition (such as gelatin) as by coacervation; or components for forming a polymer wall around a liquid perfumed center such as a ureaformaldehyde prepolymer.

Our invention also relates to the utilization of controlled release technology for the controlled release of perfumes into gaseous environments from polymers such as mixtures of epsilon polycaprolactone polymers and polyethylene which poly epsilon caprolactone polymers are defined according to at least one of the structures:

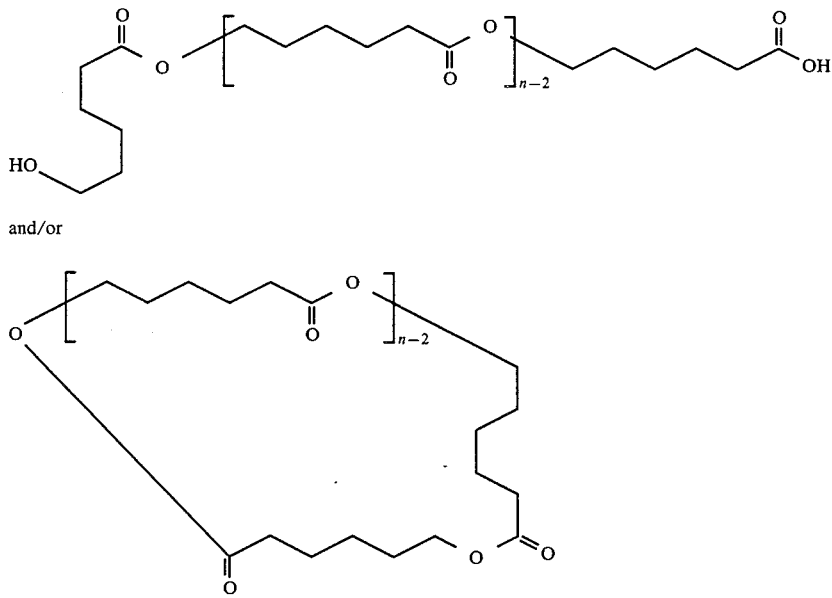

and/or wherein "n" is from about 50 up to about 1,200 with the proviso that the average "n" in the system varies from about 150 up to about 700 according to the mathematical statement:

$$[700 \geq \bar{n} \geq 150]$$

with the term $\bar{n}$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_t/dt = k_1 e^{-k_2 t}$$

wherein $k_1$ and $k_2$ are constants. According to Kydonieus, "Controlled Release Technologies: Methods, Theory, and Applications" (cited, supra, the amount of perfume composition released is proportional to time as long as the concentration of perfume material present, e.g, the ether carboxaldehydes of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the ether carboxaldehydes of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such hydroquinone or compounds having the formula:

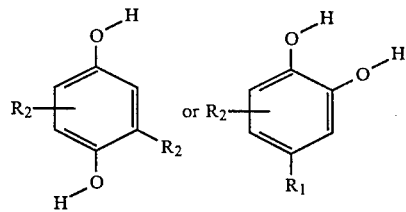

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method for incorporationg the polyhydroindan carboxaldehydes of our invention or perfume compositions containing same into the polymers may be according to the teachnique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with one of the polyhydroindan carboxaldehydes of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700:polyethylene in molten form is admixed with a high percentage of one of the polyhydroindan carboxaldehydes of our invention and mixture is solidified in the form of pellets or beads. These pellets or beads thus contain a high percentage of polyhydroindan carboxaldehydes (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention at least one of the polyhydroindan carboxaldehyde of our invention is added to the polymer in a large closed container or drum which is maintained under controlled temperature conditions while the polymer in a melted condition is mixed with at least one of the polyhydroindan carboxaldehydes of our invention under agitation.

The following Examples I–IX serve to illustrate processes for preparing the polyhydroindan carboxaldehydes of our invention. The examples following Example IX are illustrative of the organoleptic utilities of the polyhydroindan carboxaldehydes of our invention. All parts and percentages given herein are by weight unless otherwise specified.

EXAMPLE I

PREPARATION OF HYDROXY DICYCLOPENTANAL

Reaction:

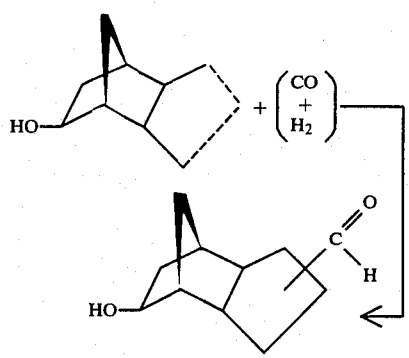

Into a 1-liter autoclave in place 0.1 grams of rhodium aceto acetate, 300 grams of dicyclopentadiene and 500 ml toluene. The autoclave is sealed and pressurized with a 50:50 (mole:mole) mixture of carbon monoxide and hydrogen to 400 psig at a temperature of 70° C. and maintained at that pressure and temperature for a period of 3.5 hours. At the end of the 3.5 hour period, the autoclave is cooled and opened, the contents are filtered and distilled on a 3" stone packed column yielding the following fractions:

| Fraction No. | Vapor Temp. (°C.) | Liquid Temp. (°C.) | Vacuum mm/Hg. Pressure (gms.) |
|---|---|---|---|
| 1 | 37/146 | 72/175 | 2.0/8.0 |
| 2 | 150 | 180 | 6.0 |
| 3 | 151 | 190 | 6.0 |
| 4 | 125 | 225 | |

Figure 1:
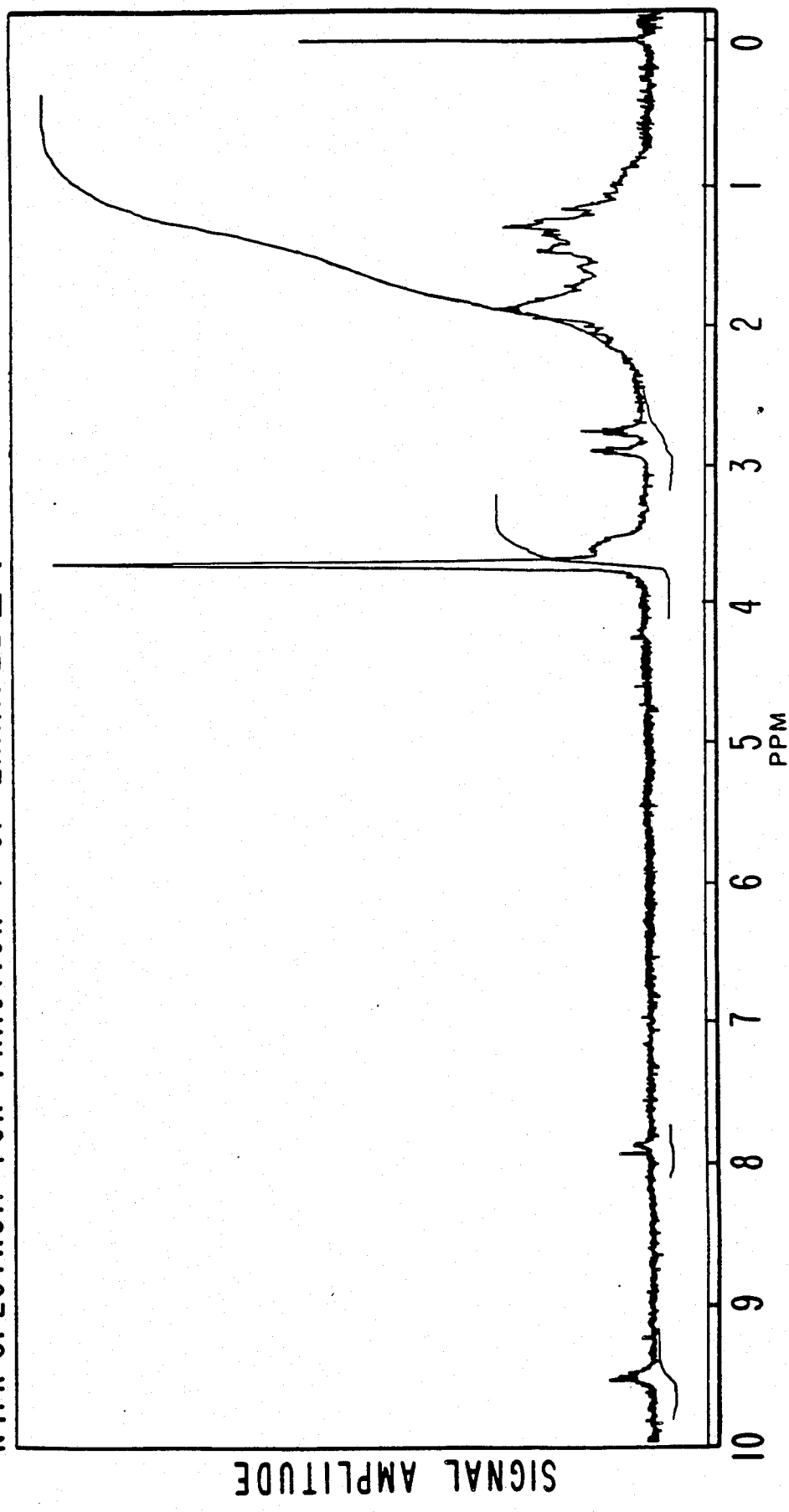
FIG. 1 is the NMR spectrum for Fraction 4 of the distillation product of the reaction product of Example I containing a mixture of compounds defined according to the structure.

FIG. 1 is the NMR spectrum for Fraction 4 of the foregoing distillation containing the compounds defined according to the structure:

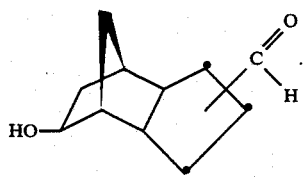

FIG. 2 is the infra-red spectrum for Fraction 4 of the foregoing distillation containing the compounds defined according to the structure:

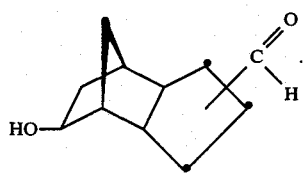

EXAMPLE II

PREPARATION OF METHOXYDICYCLOPENTENE

Reaction:

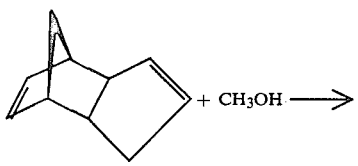 + CH$_3$OH $\longrightarrow$

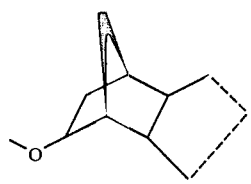

wherein in the resulting mixture in each of the molecules one of the dashed lines is a carbon-carbon double bond and the other of the dashed lines is a carbon-carbon single bond.

Into a 3-liter reaction flask equipped with stirrer, thermometer, reflux condensor, heating mantle and addition funnel is placed 600 grams of anhydrous methyl alcohol and 60 ml boron trifluoride etherate. The resulting mixture is heated to reflux. While refluxing, 1,000 grams of dicyclopentadiene is added to the reaction mass over a period of one hour. The reaction mass is then continued to be refluxed for a period of three hours, at which time 25 grams of para toluene sulfonic acid is added. The reaction mass is continued to be refluxed for a period of two hours at which time, 20 grams of sulfuric acid is added. The reaction mass is continued to be refluxed for a period of eight hours at which time, an additional 50 grams of sulfuric acid is added. The reaction mass is refluxed for a period of seven hours. The reaction mass is then cooled to room temperature and washed with 1-liter of water followed by one volume of a 5% aqueous sodium hydroxide solution.

The reaction mass is then distilled on a 12" Goodloe column to yield the following fractions:

| Fraction No. | Vapor Temp. (°C.) | Liquid Temp. (°C.) | Vacuum mm/Hg. Pressure (gms.) |
|---|---|---|---|
| 1 | 58/92 | 117/120 | 1.5/1.5 |
| 2 | 95 | 122 | 1.5 |
| 3 | 95 | 125 | 1.5 |
| 4 | 96 | 125 | 1.5 |
| 5 | 97 | 127 | 1.3 |
| 6 | 97 | 130 | 1.3 |
| 7 | 97 | 130 | 1.3 |
| 8 | 97 | 133 | 1.3 |
| 9 | 97 | 155 | 1.3 |
| 10 | 97 | 160 | 1.3 |
| 11 | 96 | 210 | 1.3 |

FIG. 3 is the GLC profile for the crude reaction product containing the compounds defined according to the structure:

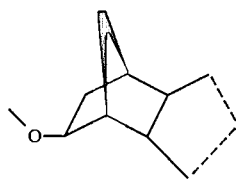

(a mixture wherein in the mixture in each of the molecules one of the dashed lines is a carbon-carbon double bond and the other of the dashed lines is a carbon-carbon single bond).

FIG. 4 is the NMR spectrum for the mixture of compounds defined according to the structure:

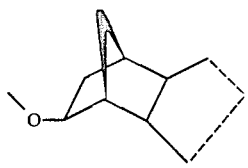

(wherein in the mixture in each of the molecules one of the dashed lines is a carbon-carbon double bond and the other of the dashed lines is a carbon-carbon single bond).

FIG. 5 is the infra-red spectrum for the mixture of compounds defined according to the structure:

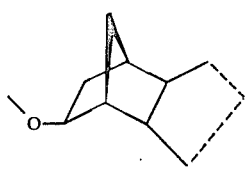

(wherein in the mixture in each of the molecules one of the dashed lines is a carbon-carbon double bond and the other of the dashed lines is a carbon-carbon single bond).

EXAMPLE III

PREPARATION OF OXO-METHOXY-DICYCLOPENTADIENE

Reaction:

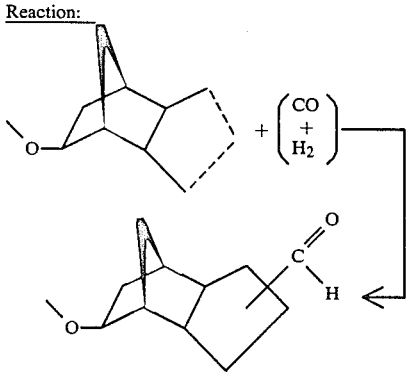

(wherein the structure containing the dashed lines is indicative of a mixture, and in the mixture in each of the molecules one of the dashed lines is a carbon-carbon double bond and the other of the dashed lines is a carbon-carbon single bond).

Into a 500 cc autoclave is placed 300 grams of the methoxy dicyclopentadiene mixture produced according to Example II and 0.1 grams of rhodium aceto acetate. The autoclave is closed and sealed and heated to 120° C. while being pressurized to 1,000 psig using a 50:50 mole:mole mixture of carbon monoxide and hydrogen. The contents of the autoclave is maintained at 1,000 psig and 120° C. for a period of twelve hours with stirring.

At the end of the twelve hour period, the autoclave is cooled and opened and the contents are distilled on a 4" splash column yielding the following fractions:

| Fraction No. | Vapor Temp. (°C.) | Liquid Temp. (°C.) | Vacuum mm/Hg. Pressure (gms.) |
|---|---|---|---|
| 1 | 95/99 | 114/115 | 2.5 |
| 2 | 119 | 125 | 2.4 |
| 3 | 124 | 135 | 3.0 |
| 4 | 125 | 150 | 2.6 |
| 5 | 144 | 230 | 2.6 |

FIG. 6 is the NMR spectrum for the mixture of compounds defined according to the structure:

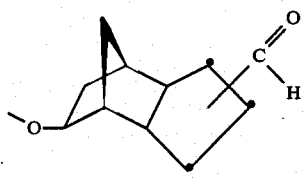

(conditions: Field strength: 100 Mhz; Solvent: CFCl₃).

FIG. 7 is the infra-red spectrum for the mixture of compounds defined according to the structure:

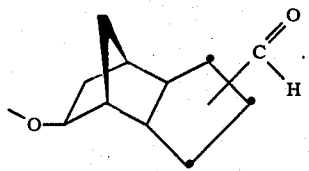

EXAMPLE IV

PREPARATION OF OXO-METHOXY-DICYCLOPENTADIENE

Reaction:

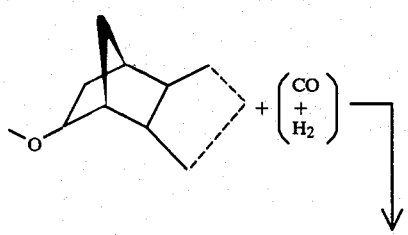

-continued
Reaction:

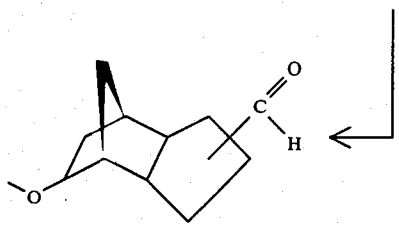

(wherein a structure containing the dashed lines is indicative of a mixture and in the mixture in each of the molecules, one of the dashed lines is a carbon-carbon double bond and the other of the dashed lines is a carbon-carbon single bond).

Into a 2,000 cc autoclave is placed 1,000 grams of methoxy-dicyclopentadiene mixture produced according to Example II which is a mixture of compounds having the structures:

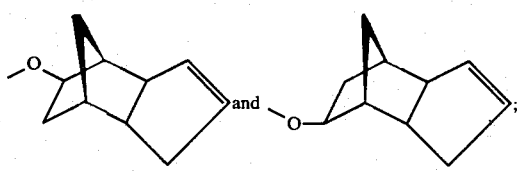

0.15 grams of rhodium (III) trichloride hydrate and 5.0 grams of triphenyl phosphine.

The autoclave is sealed and heated to 140° C. while simultaneously being pressurized to 1,000 psig using a 50:50 mole:mole mixture of carbon monoxide and hydrogen. The autoclave is stirred for a period of fifty hours at 140° C. and 1,000 psig while continuously maintaining the pressure using the carbon monoxide hydrogen mixture. At the end of the reaction the autoclave contents are cooled and the autoclave is opened and the contents are filtered and distilled on a 4" splash column yielding the following fractions:

| Fraction No. | Vapor Temp. (°C.) | Liquid Temp. (°C.) | Vacuum mm/Hg. Pressure (gms.) |
|---|---|---|---|
| 1 | 60/69 | 95/114 | 1.8 |
| 2 | 134 | 152 | 2.6 |
| 3 | 124 | 154 | 2.6 |
| 4 | 140 | 225 | 3.6. |

Fractions 2–4 are bulked and redistilled on a 24" Goodloe column yielding the following fractions:

| Fraction No. | Vapor Temp. (°C.) | Liquid Temp. (°C.) | Vacuum mm/Hg. Pressure (gms.) |
|---|---|---|---|
| 1 | 75/ | 117/ | 4.0 |
| 2 | 107 | 134 | 5.0 |
| 3 | 127 | 136 | 4.8 |
| 4 | 131 | 137 | 4.9 |
| 5 | 132 | 138 | 4.9 |
| 6 | 134 | 140 | 5.0 |
| 7 | 135 | 140 | 5.0 |
| 8 | 134 | 140 | 4.9 |
| 9 | 134 | 140 | 4.9 |
| 10 | 134 | 140 | 4.9 |

-continued

| Fraction No. | Vapor Temp. (°C.) | Liquid Temp. (°C.) | Vacuum mm/Hg. Pressure (gms.) |
|---|---|---|---|
| 11 | 134 | 142 | 4.9 |
| 12 | 134 | 146 | 4.9 |
| 13 | 134 | 160 | 4.9 |
| 14 | 134 | 195 | 4.9 |
| 15 | 125 | 220 | 4.9. |

FIG. 8 is the GLC profile for the crude reaction product containing the mixture of compounds defined according to the structure:

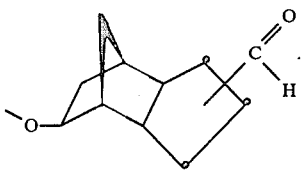

FIG. 9 is the NMR spectrum for the mixture of compounds defined according to the structure:

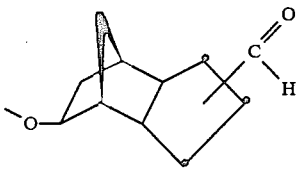

(conditions: Field strength: 100 MHz; Solvent: CFCl₃).

FIG. 10 is the infra-red spectrum for Fraction 8 of the foregoing distillation containing the mixture of compounds having the structure:

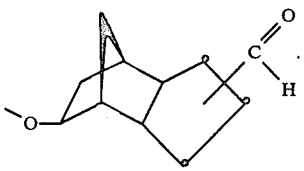

EXAMPLE V

PREPARATION OF ISOPROPOXY DICYCLOPENTADIENE

Reaction:

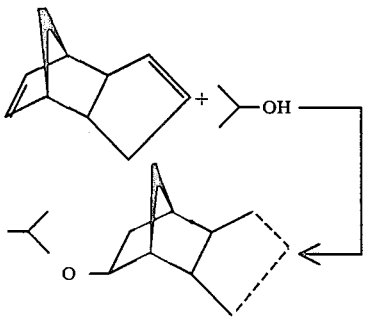

(wherein the structure containing the dashed lines is indicative of a mixture and in the mixture in each of the molecules, one of the dashed lines is a carbon-carbon double bond and the other of the dashed lines is a carbon-carbon single bond).

Into a 3-liter reaction flask equipped with thermometer, reflux condensor, addition funnel and heating mantle is placed 600 grams of anhydrous isopropyl alcohol and 30 ml of boron trifluoride etherate.

The resulting mixture is heated to reflux and while refluxing, 1100 grams of dicyclopentadiene is slowly added to the reaction mass. The reaction mass is then refluxed at 80° C. for a period of four hours at which point and time, 50 ml of an additional amount of boron trifluoride etherate is added to the reaction mass. The reaction mass is then refluxed for an additional period of ten hours, after which time, it is cooled and admixed with 1-liter of water and then washed with an equal volume of 5% aqueous sodium hydroxide. The reaction mass is then distilled on a 4" splash column yielding the following fractions:

| Fraction No. | Vapor Temp. (°C.) | Liquid Temp. (°C.) | Vacuum mm/Hg. Pressure (gms.) |
|---|---|---|---|
| 1 | 55/59 | 80/90 | 10.0 |
| 2 | 57 | 90 | 10.0 |
| 3 | 50 | 93 | 5.0 |
| 4 | 57 | 95 | 4.0 |
| 5 | 53 | 87 | 0.8 |
| 6 | 52 | 92 | 0.8 |
| 7 | 52 | 70 | 0.8 |
| 8 | 42 | 150 | 0.8. |

FIG. 11 is the GLC profile for the crude reaction product containing a mixture of compounds defined according to the structures:

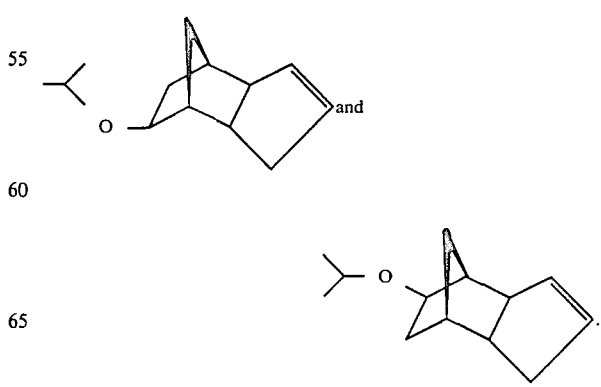

EXAMPLE VI

PREPARATION OF OXO-ISOPROPOXY DICYCLOPENTADIENE

Reaction:

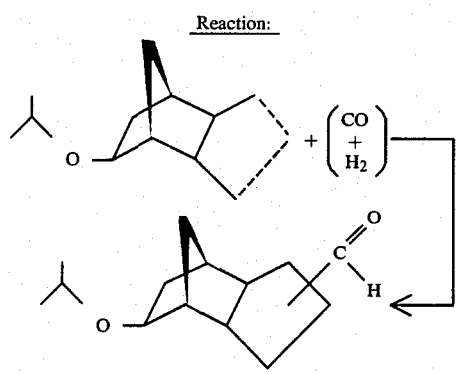

(wherein the structure containing the dashed lines is indicative of a mixture of molecules and in each of the molecules, one of the dashed lines is a carbon-carbon double bond and the other of the dashed lines is a carbon-carbon single bond).

Into a 500 cc autoclave is placed 300 grams of isopropoxy dicyclopentene, a mixture containing compounds having the structures:

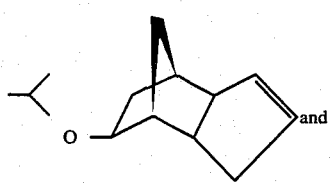

and

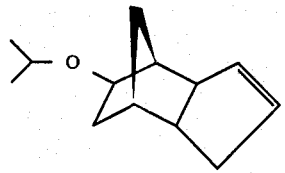

and 0.1 grams of rhodium acetoacetate. The autoclave is sealed and heated to 120° C. while simultaneously being pressurized to 1,000 psig using a 50:50 mole:mole mixture of carbon monoxide and hydrogen. The pressure is maintained at 1,000 psig with the carbon monoxide-hydrogen mixture and stirred for a period of twelve hours. At the end of the twelve hour period, the autoclave is cooled and opened and the contents filtered and distilled through a 2" splash column yielding the following fractions:

| Fraction No. | Vapor Temp. (°C.) | Liquid Temp. (°C.) | Vacuum mm/Hg. Pressure (gms.) | Weight of Fraction |
|---|---|---|---|---|
| 1 | 95/99 | 114/115 | 2.5 | 12.0 |
| 2 | 119 | 125 | 2.4 | 62.7 |
| 3 | 124 | 135 | 3.0 | 94.8 |
| 4 | 125 | 150 | 2.6 | 71.5 |
| 5 | 144 | 230 | 2.6 | 42.8. |

Fractions 2-5 are bulked and redistilled on a 12" Goodloe column yielding the following fractions:

| Fraction No. | Vapor Temp. (°C.) | Liquid Temp. (°C.) | Vacuum mm/Hg. Pressure (gms.) | Weight of Fraction |
|---|---|---|---|---|
| 1 | 69/67 | 128/135 | 1.6/1.2 | 12.1 |
| 2 | 95 | 135 | 1.0 | 8.1 |
| 3 | 102 | 126 | 1.0 | 9.1 |
| 4 | 106 | 136 | 1.0 | 6.3 |
| 5 | 106 | 136 | 1.0 | 23.7 |
| 6 | 106 | 137 | 1.0 | 23.5 |
| 7 | 108 | 137 | 1.0 | 23.8 |
| 8 | 110 | 140 | 0.9 | 26.4 |
| 9 | 121 | 150 | 0.9 | 29.5 |
| 10 | 120 | 150 | 0.9 | 24.1 |
| 11 | 118 | 159 | 0.9 | 22.9 |
| 12 | 114 | 205 | 0.9 | 15.9. |

FIG. 12 is the GLC profile for the crude reaction product prior to the distillation (conditions: SE-30 column, programmed at 80°-220° C. at 10° C. per minute).

FIG. 13 is the NMR spectrum for Fraction 8 of the foregoing distillation containing the compounds having the structure:

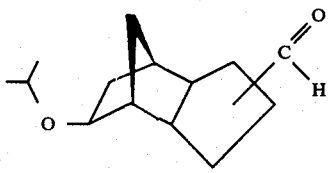

(conditions: Field strength: 100 MHz; Solvent: CFCl₃).

FIG. 14 is the infra-red spectrum for Fraction 8 of the foregoing distillation containing the compounds having the structure:

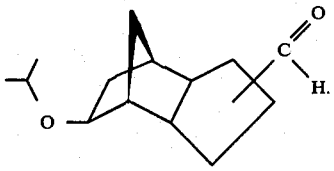

EXAMPLE VII

PREPARATION OF VERDYL ALDEHYDE

Reaction:

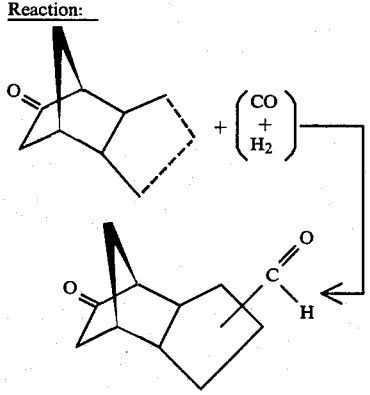

(wherein the structure having the dashed lines is indicative of a mixture and in the mixture, in each of the molecules, one of the dashed lines is a carbon-carbon double bond and the other of the dashed lines is a carbon-carbon single bond).

Into a 500 cc autoclave is placed 300 grams of "verdyl ketone", a mixture defined according to the structure:

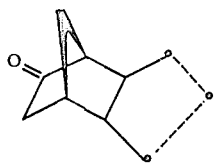

wherein in the mixture one of the dashed lines is a carbon-carbon double bond and the other of the dashed lines is a carbon-carbon single bond, 0.1 grams of rhodium acetoacetate and 5 grams of triphenyl phosphine. The autoclave is sealed and heated to 140°-160° C. while being pressurized to 1,000 psig using a 50:50 mole:mole mixture of carbon monoxide and hydrogen. The autoclave contents are maintained at 140°-160° C. for a period of ten hours at a pressure of 1,000 psig as maintained by adding additional amounts of 50:50 mole:mole mixture of carbon monoxide and hydrogen. At the end of the ten hour period, the autoclave is cooled to room temperature and opened and the contents are filtered and distilled on a 12" Goodloe column yielding the following fractions:

| Fraction No. | Vapor Temp. (°C.) | Liquid Temp. (°C.) | Vacuum mm/Hg. Pressure (gms.) | Reflux Ratio R/D |
|---|---|---|---|---|
| 1 | 65/67 | 125/130 | 1.4 | 4:1/ |
| 2 | 65 | 137 | 1.4 | 1.4 |
| 3 | 75 | 152 | 1.4 | 4:1 |
| 4 | 117 | 158 | 1.4 | 4:1 |
| 5 | 124 | 160 | 1.4 | 4:1 |
| 6 | 138 | 180 | 1.7 | 4:1 |
| 7 | 138 | 185 | 1.8 | 4:1 |
| 8 | 140 | 208 | 2.0 | 1:1 |
| 9 | 150 | 240 | 2.8 | 1:1. |

FIG. 15 is the GLC profile for the crude reaction product of Example VII (prior to distillation) containing the mixture of compounds defined according to the structure:

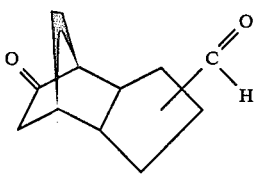

as well as the starting material defined according to the structure:

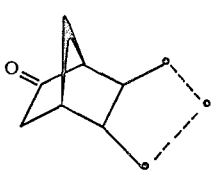

(wherein in the mixture, one of the dashed lines is a carbon-carbon double bond and the other of the dashed lines is a carbon-carbon single bond). The peak indicated by reference numeral "150" is the peak for the mixture of compounds defined according to the structure:

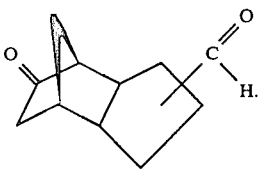

The peak indicated by reference numeral "151" is the peak for the mixture of compounds defined according to the structure:

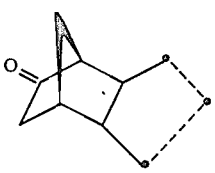

(wherein in the mixture in each of the molecules, one of the dashed lines is a carbon-carbon double bond and the other of the dashed lines is a carbon-carbon single bond).

FIG. 16 is the NMR spectrum for the mixture of compounds defined according to the structure:

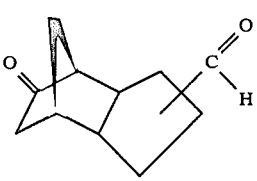

(conditions: Field strength: 100 MHz; Solvent: $CFCl_3$).

FIG. 17 is the infra-red spectrum for Fraction 7 of the foregoing distillation containing a mixture of compounds defined according to the structure:

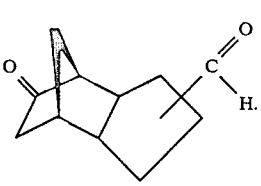

EXAMPLE VIII

PREPARATION OF "OXOCYCLACET"

Reaction:

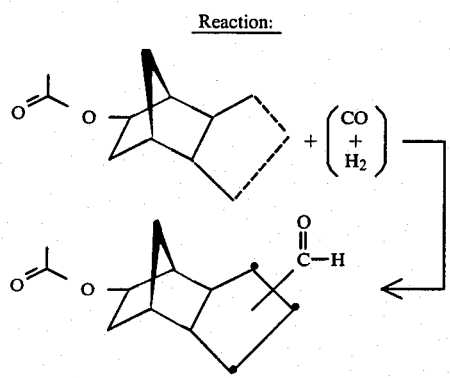

(wherein the structure having dashed lines is indicative of a mixture of compounds wherein in the mixture in each of the molecules one of the dashed lines represents a carbon-carbon double bond and the other of the dashed lines represents a carbon-carbon single bond).

Into a 2,000 cc autoclave is placed 484 grams of "cyclacet", a mixture of compounds defined according to the structure:

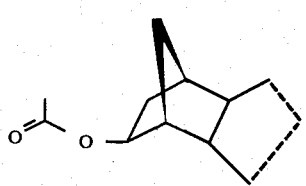

(wherein in the mixture in each of the molecules, one of the dashed lines is a carbon-carbon double bond and the other of the dashed lines is a carbon-carbon single bond; wherein in the mixture in each of the molecules one of the dashed lines is a carbon-carbon double bond and the other of the dashed lines is a carbon-carbon single bond; 4 grams of triphenyl phosphine; 0.4 grams of rhodium-carbonyl-ditriphenyl phosphine chloride and 100 ml toluene).

The autoclave is sealed and heated to 180° C. while simultaneously being pressurized to 1,000 psig using a 50:50 mole:mole mixture of carbon monoxide and hydrogen. The contents of the autoclave are maintained at 180° C. and 1,000 psig using the carbon monoxide and hydrogen mixture to keep the pressure at 1,000 psig and maintained at that temperature and pressure for twelve hours. At the end of the twelve hour period, the autoclave is cooled to room temperature and opened. The contents are filtered and the filtrate is distilled on a 12" Goodloe column yielding the following fractions:

| Fraction No. | Vapor Temp. (°C.) | Liquid Temp. (°C.) | Vacuum mm/Hg. Pressure (gms.) |
|---|---|---|---|
| 1 | 112/98 | 155/152 | 6.0/3.5 |
| 2 | 98 | 157 | 3.0 |
| 3 | 138 | 159 | 3.0 |
| 4 | 145 | 173 | 3.0 |
| 5 | 140 | 178 | 3.0 |
| 6 | 140 | 195 | 3.0 |

-continued

| Fraction No. | Vapor Temp. (°C.) | Liquid Temp. (°C.) | Vacuum mm/Hg. Pressure (gms.) |
|---|---|---|---|
| 7 | 144 | 230 | 3.0. |

GLC, NMR and IR analyses yield the information that the resulting product is a mixture of compound having the structure:

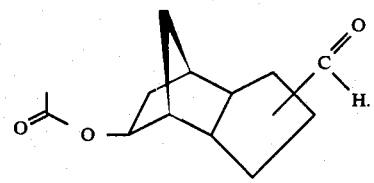

FIG. 18 is the GLC profile for Fraction 4 of the foregoing distillation containing the compounds having the structure:

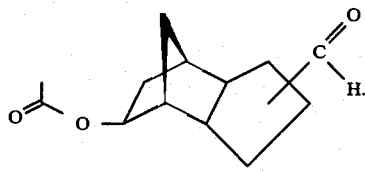

FIG. 19 is the infra-red spectrum for the mixture of compounds produced according to this example defined according to the structure:

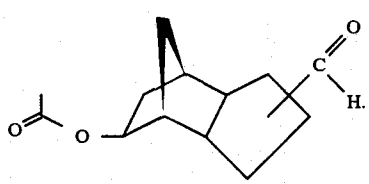

EXAMPLE IX

PREPARATION OF OXO-METHYLCYCLOPENTADIENE DIMERS

Reaction:

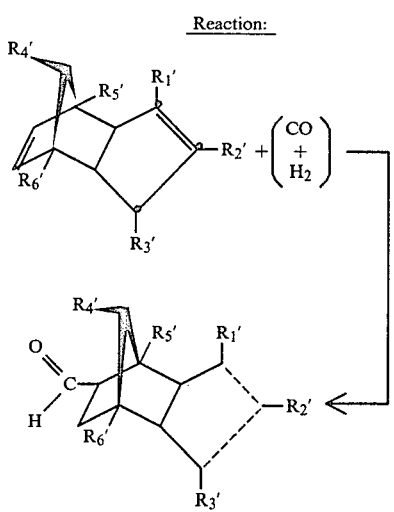

(wherein the structure containing the dashed lines is indicative of a mixture and in the mixture in each of the molecules one of the dashed lines is a carbon-carbon double bond and the other of the dashed lines is a carbon-carbon single bond; and wherein in the structures containing $R_1'$, $R_2'$, $R_3'$, $R_4'$, $R_5'$ and $R_6'$, these structures are indicative of mixtures and in the mixtures, in each of the molecules, one of $R_4'$, $R_5'$ and $R_6'$ is methyl and the other of $R_4'$, $R_5'$ and $R_6'$ are hydrogen; and one of $R_1'$, $R_2'$ and $R_3'$ is methyl and the other of $R_1'$, $R_2'$ and $R_3'$ are hydrogen).

Into a 2,000 cc autoclave is placed 1,000 grams of methyldicyclopentadiene dimer having the structure:

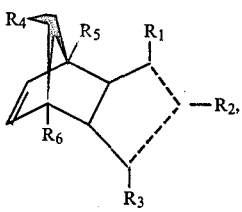

(a mixture wherein, in the mixture in each of the molecules one of the dashed lines represents a carbon-carbon double bond and the other of the dashed lines represents a carbon-carbon single bond; wherein one of $R_1$, $R_2$ and $R_3$ is methyl and the other of $R_1$, $R_2$ and $R_3$ are hydrogen; and wherein one of $R_4$, $R_5$ and $R_6$ is methyl and the other of $R_4$, $R_5$ and $R_6$ are hydrogen); and 0.15 grams of rhodium (III) trichloride-triphenyl phosphine.

The autoclave is sealed and heated to 140° C. while simultaneously pressurizing the contents to 1,000 psig using a 50:50 mole:mole mixture of carbon monoxide and hydrogen. While maintaining the temperature of 140° C. and the pressure at 1,000 psig using the carbon monoxide-hydrogen mixture, the autoclave is stirred for a period of nine hours. At the end of the nine hour period, the autoclave contents are cooled and the autoclave is opened and the contents are filtered. The resulting filtrate is distilled on a 2" splash column yielding the following fractions:

| Fraction No. | Vapor Temp. (°C.) | Liquid Temp. (°C.) | Vacuum mm/Hg. Pressure (gms.) | Weight of Fraction |
|---|---|---|---|---|
| 1 | 53/68 | 74/85 | 1.1/1.0 | 21.4 |
| 2 | 68 | 85 | 1.0 | 83.5 |
| 3 | 80 | 95 | 3.2 | 137.4 |
| 4 | 85 | 107 | 5.0 | 110.2 |
| 5 | 95 | 107 | 3.6 | 100.2 |
| 6 | 110 | 118 | 4.9 | 109.5 |
| 7 | 121 | 125 | 5.5 | 93.2 |
| 8 | 125 | 127 | 6.0 | 120.2 |
| 9 | 125 | 130 | 6.1 | 109.0 |
| 10 | 110 | 140 | 2.2 | 161.1 |

FIG. 20 is the GLC profile for the crude reaction product containing the compounds defined according to the structure:

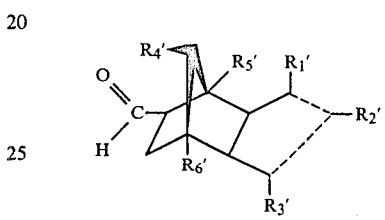

(a mixture wherein the mixture one of the dashed lines is a carbon-carbon double bond and the other of the dashed lines is a carbon-carbon single bond; wherein one of $R_1'$, $R_2'$ and $R_3'$ is methyl and the other of $R_1'$, $R_2'$ and $R_3'$ are hydrogen; and wherein one of $R_4'$, $R_5'$ and $R_6'$ is methyl and the other of $R_4'$, $R_5'$ and $R_6'$ are hydrogen).

FIG. 21 is the GLC profile for Fraction 9 of the foregoing distillation containing the compounds having the structure:

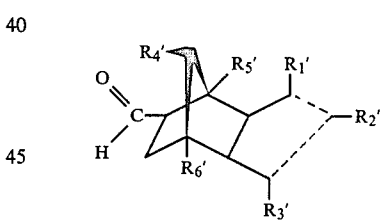

(a mixture wherein in the mixture one of the dashed lines is a carbon-carbon double bond and the other of the dashed lines is a carbon-carbon single bond; wherein one of $R_1'$, $R_2'$ and $R_3'$ is methyl and the other of $R_1'$, $R_2'$ and $R_3'$ are hydrogen and wherein one of $R_4'$, $R_5'$ and $R_6'$ is methyl and the other of $R_4'$, $R_5$, and $R_6'$ are hydrogen).

FIG. 22 is the NMR spectrum for Fraction 9 of the foregoing distillation containing a mixture of compounds defined according to the structure:

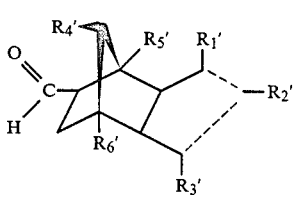

(a mixture wherein in the mixture in each of the molecules one of the dashed lines is a carbon-carbon double bond and the other of the dashed lines is a carbon-carbon single bond; and wherein one of $R_1'$, $R_2'$ and $R_3'$ is methyl and the other of $R_1'$, $R_2'$ and $R_3'$ are hydrogen and wherein one of $R_4'$, $R_5'$ and $R_6'$ is methyl and the other of $R_4'$, $R_5'$ and $R_6'$ are hydrogen). (Conditions: Field strength: 100 MHz; Solvent: CFCl$_3$).

FIG. 23 is the infra-red spectrum for Fraction 9 of the foregoing distillation containing a mixture of compounds defined according to the structure:

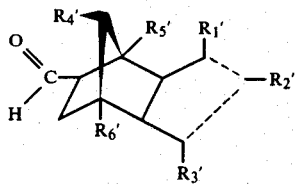

(a mixture wherein in the mixture one of the dashed lines is a carbon-carbon double bond and the other of the dashed lines is a carbon-carbon single bond and wherein one of $R_1'$, $R_2'$ and $R_3'$ is methyl and the other of the $R_1'$, $R_2'$ and $R_3'$ are hydrogen and wherein one of $R_4'$, $R_5'$ and $R_6'$ is methyl and the other of $R_4'$, $R_5'$ and $R_6'$ are hydrogen).

EXAMPLE X

FLORAL PERFUME COMPOSITIONS

A mixture of compounds having the structure:

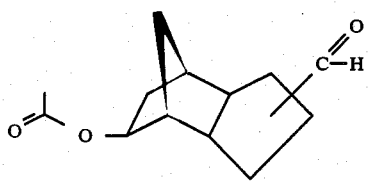

produced according to Example VIII has a floral, woody aroma. This material has great warmth and richness and blends well with many floral concepts. It is a rather unique floral note of great value to perfumery. Its use may be demonstrated by a floral fragrance set forth, infra whereby this mixture is used to the extent of 5% by weight.

A mixture of compounds defined according to the structure:

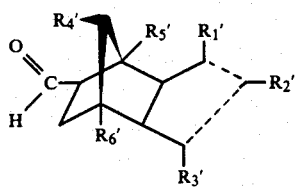

wherein one of the dashed lines is a carbon-carbon double bond and the other of the dashed lines is a carbon-carbon single bond; wherein one of $R_1'$, $R_2'$ or $R_3'$ is methyl and the other of $R_1'$, $R_2'$ and $R_3'$ are hydrogen; and wherein one of $R_4'$, $R_5'$ and $R_6'$ is methyl and the other of $R_4'$, $R_5'$ and $R_6'$ is hydrogen produced according to Example IX imparts to this floral fragrance a fresh, eucalyptus, balsamic and green aroma causing it to be quite useful in "fresh air aroma" type fragrances. The addition of this mixture imparts a very desirable fresh air character.

The mixture of compounds defined according to the structure:

produced according to Example III as well as Example IV imparts to the floral formulation a woody, piney, green and ozoney aroma profile with green and twigging undertones.

The mixture of compounds defined according to the structure:

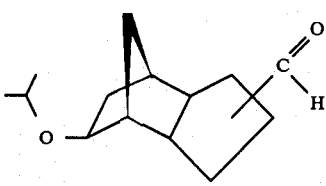

produced according to Example VI imparts to this floral formulation a twiggy, green and ozoney aroma profile with woody and green undertones.

The mixture of compounds defined according to the structure:

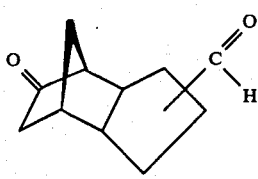

produced according to Example VII imparts to this floral formulation a cinnamon-like and green aroma with green and woody undertones.

All five of these products perform quite well in fragrances and are judged to be very valuable fragrance materials by an independent bench panel of fiver perfumers (independent of the inventors or the assignee of the instant application for letters patent):

| | FLORAL FRAGRANCE | | | | |
|---|---|---|---|---|---|
| Example: | "X(A)" | "X(B)" | "X(C)" | "X(D)" | "X(E)" |
| Citronellol | 12.3 | 12.3 | 12.3 | 5.0 | 5.0 |
| Geraniol | 2.5 | 2.5 | 2.5 | 5.0 | 5.0 |
| Amyl Cinnamic Aldehyde | 24.6 | 24.6 | 24.6 | 5.0 | 5.0 |
| Galaxolide ® 50 (Trademark Tricyclic Isochroman of | 9.8 | 9.8 | 9.8 | 5.0 | 5.0 |

-continued
FLORAL FRAGRANCE

| | | | | | |
|---|---|---|---|---|---|
| International Flavors & Fragrances Inc.) | | | | | |
| Vertenex High Cis (Cis-t Butylcyclohexenyl Acetate; Para Isomer) | 7.4 | 7.4 | 7.4 | 5.0 | 5.0 |
| Rose Oxide | 0.7 | 0.7 | 0.7 | 5.0 | 5.0 |
| Cinnamic Alcohol | 19.6 | 19.6 | 19.6 | 5.0 | 5.0 |
| Aldehyde C-11 (n-Undecylenic Aldehyde) | 0.5 | 0.5 | 0.5 | 5.0 | 5.0 |
| Aldehyde C-12 (n-Dodecyl Aldehyde in 10% solution in diethyl phthalate) | 0.5 | 0.5 | 0.5 | 5.0 | 5.0 |
| Citronellal (10% solution in diethyl phthalate) | 0.5 | 0.5 | 0.5 | 5.0 | 5.0 |
| Phenyl Ethyl Acetate | 2.5 | 2.5 | 2.5 | 5.0 | 5.0 |
| Ylang Oil | 1.2 | 1.2 | 1.2 | 5.0 | 5.0 |
| Indisan (hydrogenated derivative of reaction product of Camphene and Resorcinol) | 3.7 | 3.7 | 3.7 | 5.0 | 5.0 |
| Musk Ketone | 5.0 | 5.0 | 5.0 | 5.0 | 5.0 |
| Oakmoss Resin | 0.5 | 0.5 | 0.5 | 5.0 | 5.0 |
| Liatrix Absolute (10% in diethyl phthalate) | 2.5 | 2.5 | 2.5 | 5.0 | 5.0 |
| Vetiver Acetate | 1.2 | 1.2 | 1.2 | 5.0 | 5.0 |
| Diethyl Phthalate | 5.0 | 5.0 | 5.0 | 5.0 | 5.0 |
| Example: | X(A) | X(B) | X(C) | X(D) | X(E) |

Mixture defined according to the structure:    5.0   0   0   0   0

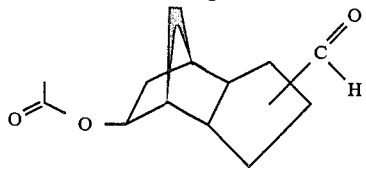

produced according to Example VIII.

Mixture defined according to the structure:    0   5.0   0   0   0

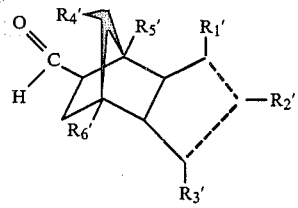

produced according to Example IX.

Mixture defined according to the structure:    0   0   5.0   0   0

produced according to Example III or IV.

Mixture defined according to the structure:    0   0   0   5.0   0

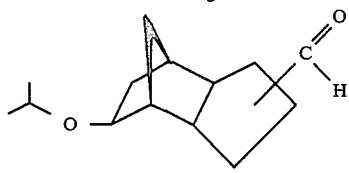

produced according to Example VI

Mixture defined according to the structure:    0   0   0   0   5.0

| FLORAL FRAGRANCE |
|---|
| 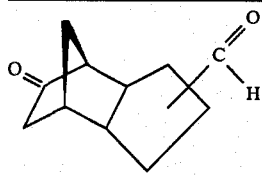 |
| produced according to Example VII. |

The mixture defined according to the structure:

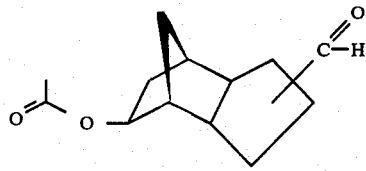

prepared according to Example VIII causes this fragrance to be described as "a floral fragrance with intense, woody undertones".

The mixture defined according to the structure:

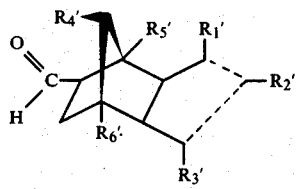

prepared according to Example IX causes this fragrance to be described as a "floral fragrance with fresh, eucalyptus, balsamic and green undertones and a general "fresh air" character".

The mixture defined according to the structure:

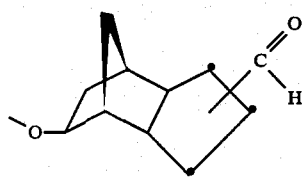

prepared according to Example III or Example IV causes the fragrance to be described as "a floral aroma with woody, piney, green and ozoney topnotes and green and twiggy undertones".

The mixture defined according to the structure:

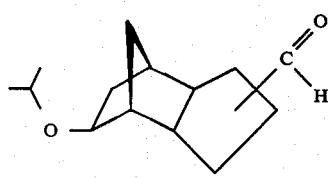

prepared according to Example VI causes the fragrance thus produced to be described as "a floral aroma with twiggy, green and ozoney topnotes and woody and green undertones".

The mixture defined according to the structure:

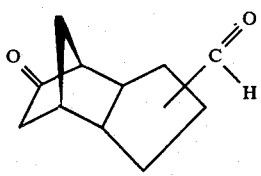

prepared according to Example VII causes the fragrance produced using same to be described as "a floral aroma with cinnamon-like and green topnotes and green and woody undertones".

EXAMPLE XI

PREPARATION OF COSMETIC POWDER COMPOSITIONS

Cosmetic powder compositions are preapred by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| Mixture defined according to the structure:<br><br>produced according to Example VIII. | A floral and woody aroma. |
| Mixture defined according to the structure:<br><br>produced according to Example IX. | A fresh eucalyptus, balsamic and green aroma profile. |

TABLE II-continued

| Substance | Aroma Description |
|---|---|
| Mixture defined according to the structure: 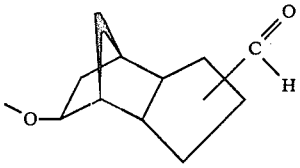 produced according to Example III or IV. | A woody, piney, green and ozoney aroma with green and twiggy undertones. |
| Mixture defined according to the structure: 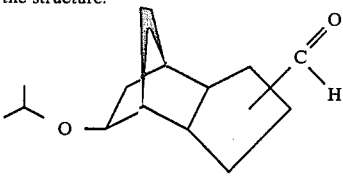 produced according to Example VI. | A twiggy, green and ozoney aroma with woody and green undertones. |
| Mixture defined according to the structure: 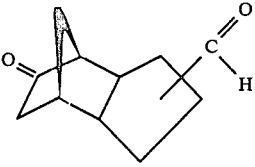 produced according to Example VII. | A cinnamon-like and green aroma with green and woody undertones. |
| Perfume composition produced according to Example X(A). | A floral fragrance with intense, woody undertones. |
| Perfume composition produced according to Example X(B). | A floral fragrance with fresh, eucalyptus, balsamic and green undertones and a general "fresh air" character. |
| Perfume composition produced according to Example X(C). | A floral aroma with woody, piney, green and ozoney topnotes and green and twiggy undertones. |
| Perfume composition produced according to Example X(D). | A floral aroma with twiggy, green and ozoney topnotes and woody and green undertones. |
| Perfume composition produced according to Example X(E). | A floral aroma with cinnamon-like and green topnotes and green and woody undertones. |

EXAMPLE XII
PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example XI are prepared containing 0.10%, 0.15%, 0.20%, 0.25%, 0.30% and 0.35% of the substance set forth in Table II of Example XI. They are prepared by adding and homogeneously mixing the appropriate quantity of substance set forth in Table II of Example XI in the liquid detergent. The detergents all possess excellent aromas as set forth in Table II of Examples XI, the intensity increasing with greater concentrations of substance as set forth in Table II of Example XI.

EXAMPLE XIII
PREPARATION OF COLOGNES AND HANDKERCHIEF PERFUMES

Compositions as set forth in Table II of Example XI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XI are imparted to the colognes and to the handkerchief perfumes at all levels indicated.

EXAMPLE IV
PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table II of Example XI until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example XI.

EXAMPLE XV
PREPARATION OF SOLID DETERGENT COMPOSITIONS

Detergents are prepared using the following ingredients according to Example I of Canadian Pat. No. 1,007,948 (incorporated herein by reference):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example XI. Each of the detergent samples has an excellent aroma as indicated in Table II of Example XI.

EXAMPLE XVI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate, coating, the outer coating and the perfuming material are as follows:
1. A water "dissolvable" paper ("Dissolvo Paper")

2. Adogen 448 (m.p. about 140° F.) as the substrate coating; and
3. An outer coating having the following formulation (m.p. about 150° F.):
   57% C$_{20-22}$ HAPS
   22% isopropyl alcohol
   20% antistatic agent
   1% of one of the substances as set forth in Table II of Example XI.

Fabric softening compositions prepared according to Example I at column 15 of U.S. Pat. No. 3,632,396 having aroma characteristics as set forth in Table II of Example XI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example XI, supra.

EXAMPLE XVII

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

|  | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example XI, Supra. | 0.10 |

The perfume substances as set forth in Table II of Example XI add aroma characteristics as set forth in Table II of Example XI which are rather intense and aesthetically pleasing to the users of the soft-feel, good-hold pump hair sprays.

EXAMPLE XVIII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produce by Armak Corporation. This material is "COMPOSITION B".

The resulting COMPOSITION A and COMPOSITION B are then mixed in a 50:50 wt ratio of A:B and cooled to 45° C. and 0.3 wt percent of perfuming substance as set forth in Table II of Example XI is added to the mixture. The resulting mixture is cooled to 40° C. and blending is carried out for an additional one hour in each case. At the end of this blending period, the resulting material has a pleasant fragrance as indicated in Table II of Example XI.

EXAMPLE XIX

Each of the fragrance materials of Table II of Example XI, supra, are added to a 50:50 weight:weight mixture of low density polyethylene:polyepsilon caprolactone PCL-700 forming pellets with scents as set forth in Table II of Example XI, supra.

75 Pounds of a 50:50 mixture of PCL-700 polyepsilon caprolactone (manufactured by the Union Carbide Corporation of New York, N.Y. having a melting point of about 180°–190° F.): Low density polyethylene, are heated to about 250° F. in a container of the kind illustrated in FIGS. 24 and 25. 25 Pounds of each of the fragrance materials as set forth in Table II of Example XI is then quickly added to the liquified polymer mixture, the lid 228 is put in place and the agitating means 273 are actuated. The temperature is then raised to about 260° F. and the mixing is continued for 5–15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table II of Example XI, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example XI, supra. The sheets of films are cut into strips of 0.25" in width×3" in length and placed into room air fresheners.

On operation of the room air freshener, after four minutes, the room in each case has an aesthetically pleasing aroma with no foul ordor being present, the aroma being described in Table II of Example XI, supra.

PATENTS INCORPORATED HEREIN BY REFERENCE

The following patents referred to supra are hereby incorporated herein by reference:
U.S. Pat. No. 3,632,396;
U.S. Pat. No. 3,948,818;

Canadian Pat. No. 1,007,948.

What is claimed is:

1. A mixture of polyhydroindan carboxaldehydes defined according to the structure:

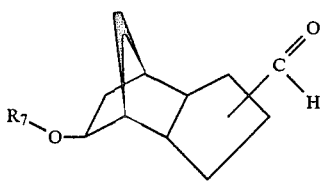

wherein R₇ represents a moiety selected from the group consisting of methyl and isopropyl prepared according to the process of reacting bicyclopentadiene having the structure:

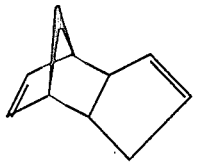

with an anhydrous alkanol having the structure:

R₇—OH in the presence of a Lewis acid catalyst at reflux conditions for a period of time in order to effect substantially complete conversion to a mixture of compounds defined according to the structure:

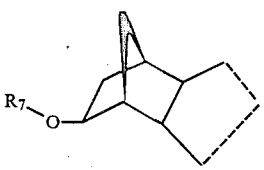

wherein the mixture in each of the compounds one of the dashed lines represents a carbon-carbon double bond and the other of the dashed lines represents a carbon-carbon single bond; then fractionally distilling the resulting reaction product in order to recover the said mixture of compounds defined according to the structure:

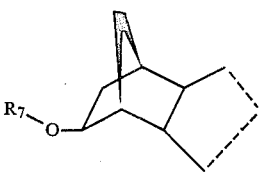

and then reacting the resulting mixture having the structure:

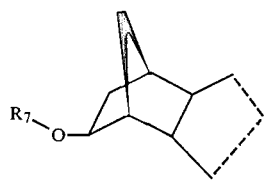

with carbon monoxide and hydrogen in the presence of an "oxo" reaction catalyst according to the reaction:

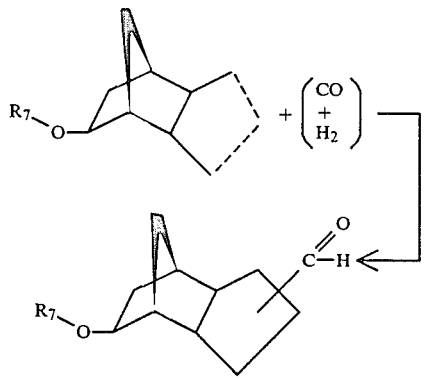

at a temperature of between 150° C. and 300° C.; at a pressure of between 20 and 250 atmospheres; with a ratio of partial pressure of carbon monoxide:partial pressure of hydrogen being from 0.1:1 up to 1:0.1.

2. A process for augmenting or enhancing the aroma of a perfume composition, cologne or perfumed article comprising the step of intimately admixing with a perfume composition base, a cologne base or a perfumed article base, an aroma augmenting or enanching quantity of the composition of matter defined according to claim 1.

3. The composition of matter of claim 1 wherein R₇ is methyl; wherein the mixture of compounds defined according to the structure:

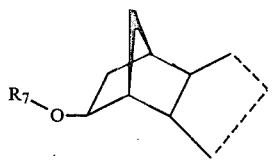

is fractionally distilled at a vapor temperature of from 58° up to 97° C. and a vacuum of from 1.3 up to 1.5 mm/Hg.; and wherein the mixture of compounds defined according to the structure:

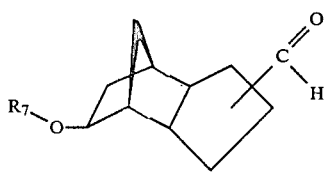

is fractionally distilled at a vapor temperature of from 124°-140° C. and a vacuum of 2.6-3.6 mm/Hg.

4. The composition of matter of claim 1 wherein R₇ is isopropyl; wherein the mixture of compounds defined according to the structure:

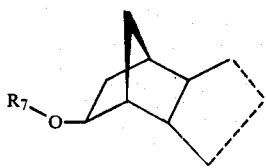

is fractionally distilled at a vapor temperature of from 42° up to 59° C. and a vacuum of from 0.8 up to 10.0 mm/Hg. pressure; and wherein the mixture of compounds defined according to the structure:

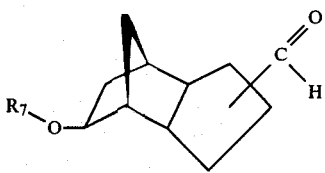

is fractionally distilled at a vapor temperature of from 119° up to 144° C. and a vacuum of from 2.4 up to 3.0 mm/Hg.

5. The composition of matter defined according to claim 1 wherein in the reaction between the bicyclopentadiene and the alkanol, the Lewis acid catalyst is boron trifluoride etherate.

6. The composition of matter of claim 1 wherein in the "oxo" reaction the "oxo" reaction catalyst is a mixture of rhodium (III) trichloride hydrate and triphenyl phosphine or the "oxo" reaction catalyst is rhodium aceto acetate.

* * * * *